(12) United States Patent
Hoge, II et al.

(10) Patent No.: US 6,855,849 B2
(45) Date of Patent: Feb. 15, 2005

(54) NON-C2-SYMMETRIC BISPHOSPHINE LIGANDS AS CATALYSTS FOR ASYMMETRIC HYDROGENATION

(75) Inventors: Garrett Stewart Hoge, II, Ann Arbor, MI (US); Om Prakash Goel, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/245,941

(22) Filed: Sep. 18, 2002

(65) Prior Publication Data

US 2003/0073868 A1 Apr. 17, 2003

Related U.S. Application Data

(63) Continuation-in-part of application No. 10/083,923, filed on Feb. 27, 2002, now Pat. No. 6,689,915.
(60) Provisional application No. 60/277,125, filed on Mar. 19, 2001.

(51) Int. Cl.$^7$ .............................. C07F 9/50; C07E 9/02; C07E 9/28
(52) U.S. Cl. .............................. 568/17; 568/8; 568/13; 568/14; 564/12; 564/15
(58) Field of Search .............................. 568/8, 17, 13, 568/14, 16; 564/12, 15

(56) References Cited

U.S. PATENT DOCUMENTS

| | | |
|---|---|---|
| 5,646,241 A | 7/1997 | Dershem et al. |
| 6,194,593 B1 | 2/2001 | Imamoto et al. |
| 6,376,715 B1 | 4/2002 | Newman et al. |

FOREIGN PATENT DOCUMENTS

| | | |
|---|---|---|
| EP | 0 997 470 A1 | 5/2000 |
| EP | 1 243 591 | 7/2003 |
| JP | 11-80179 | 3/1999 |
| JP | 2000-256384 | 9/2000 |
| JP | 2000-319288 | 11/2000 |
| WO | WO 00 11008 A | 3/2000 |
| WO | WO 00 26220 A | 5/2000 |
| WO | WO 99 62917 A | 12/2000 |

OTHER PUBLICATIONS

CA:128:244192 abs of WO 9812202 Mar. 1998.*
CA:119:271398 abs of WO 9315090 Aug. 1993.*
CA:123:112406 abs of EP643065 Mar. 1995.*
CA:120:245502 abs of JP05239076 Sep. 1993.*
CA:122:133285 abs of Tetrahedron Asymmetry by Ramsden 5(10) pp 2033–44 1994.*
CA:120:245450 abs of Inorganic Chem. by Gabbitas et al (22) pp 3271–6 1993.*
CA:135:257322 abs of JACS by Chatterjee et al (12) pp 1890–1896 2001.*
CA:125:221957 abs of Tetrahedron Letters by Cereghetti et al 37(30) 5347–5350 1996.*
CA:125:221957 abs of Tetrahedron Letters by Cereghetti et al 37 (30) pp 5347–5350 1996.*
CA:121:83460 abs of Australian Journal of Chemistry by Bowmaker et al 47(3) pp 451–60 1994.*
Ohashi, Atsushi, et al, "A New Synthetic Route to Unsymmetric P–chirogenic bisphosphine Ligands", Tetrahedon Letters, (2001), vol. 42, pp. 1099–1101.
Ohashi, Atsushi, et al, "Highly Enantioselective Hydrigenation of a–Dehydroamino Acids by Rhodium Complexes with New Unsymmetric P–Chirogenic Bisphosphine Ligands", Organic Letters, (2001), vol. 3, No. 3, pp. 373–375.
Ohashi, Atsushi, et al, "Unsymmetrical P–Chirogenic Bis(phosphane) Ligands: Their Preparation and Use in Rhodium–Catalyzed Asymmetric Hydrogentaion", Eur. J. Org. Chem., (2002), pp. 2535–2546.
Michos, D. et al., "Tungsten(VI) Hexahydride Complexes Supported by Chelating Triphosphine Ligands: Protonation To Give n2–Dihydrogen Complexes and Catalytic Dehydrogenation of Cyclooctane to Cyclooctene", Inorg. Chem., (1993), vol. 32, Pages.
CA:134:311257 abs of Tetrahedron Letters by Ohashi et al 42(6) pp 1099–1101 2001 (Abstract Only).
CA:120:152206 abs of Inorganic Chemistry by Bowmaker et al (23) pp 3593–3600 1993 (Abstract Only).
CA:133:171445 abs of Dalton by Chatterjee et al (12) pp 1829–1830 2000 (Abstract Only).
CA:91:122957 abs of Journal of Organic Chemistry by King et al 44(18) pp 3095–100 1979 (Abstract Only).
CA:75:129903 abs of Inorganic Physical and Theroretical by Dawson et al (18) pp 2897–0 1971 (Abstract Only).
CA:123:112179 abs of Journal of Chem Soc. Chem Comm. by Potyen et al (8) pp 849–51 1995 (Abstract Only).
CA:97:110089 abs of Chemistry and Industry (5) pp 163–64 by Briggs et al 1982 (Abstract Only).
CA:101:111030 abs of Tetrahedron Letts. by Kauffam et al 25(19) pp 1963–6 1984 (Abstract Only).

* cited by examiner

*Primary Examiner*—Peter O'Sullivan
(74) *Attorney, Agent, or Firm*—Matthew J. Russo

(57) ABSTRACT

Non-C$_2$-symmetric bisphospholane ligands and methods for their preparation are described. Use of metal/non-C$_2$-symmetric bisphospholane complexes to catalyze asymmetric transformation reactions to provide high enantiomeric excesses of formed compounds is also described.

2 Claims, 11 Drawing Sheets

R = t-butyl, isopropyl, adamantyl, (1,1)-dimethylpropane,
    (1,1)-diethylbutane, c-$C_5H_9$, or c-$C_6H_{11}$
$R_1$ = methyl, ethyl, isopropyl, cyclohexyl, or any alkyl
Ms = mesylate

NON-C2-SYMMETRIC BISPHOSPHINE LIGANDS AS CATALYSTS FOR ASYMMETRIC HYDROGENATION

CROSS-REFERENCE TO RELATED APPLICATIONS

This application is a continuation-in-part of Ser. No. 10/083,923, filed Feb. 27, 2002 now U.S. Pat. No. 6,689,915, which claims the benefit of provisional patent application No. 60/277,125, filed Mar. 19, 2001, the complete disclosures of which are herein incorporated by reference in their entirety.

FIELD OF THE INVENTION

This invention relates to non-$C_2$-symmetric bisphosphine (BisP) ligands and to a method for their preparation. In addition, this invention relates to forming metal/bisphosphine complexes that catalyze asymmetric transformation reactions to generate high enantiomeric excesses of formed compounds. The invention also relates to a method for preparing BisP.

BACKGROUND OF THE INVENTION

A growing trend in the pharmaceutical industry is to market chiral drugs in enantiomerically pure form to provide desired positive effects in humans. Production of enantiomerically pure compounds is important for several reasons. First, one enantiomer often provides a desired biological function through interactions with natural binding sites, but another enantiomer typically does not have the same function or effect. Further, it is possible that one enantiomer has harmful side effects, while another enantiomer provides a desired positive biological activity. To meet this demand for chiral drugs, many approaches for obtaining enantiomerically pure compounds have been explored such as diastereomeric resolution, structural modification of naturally occurring chiral compounds, asymmetric catalysis using synthetic chiral catalysts and enzymes, and the separation of enantiomers using simulated moving bed (SMB) technology.

Asymmetric catalysis is often the most efficient method for the synthesis of enantiomerically enriched compounds because a small amount of a chiral catalyst can be used to produce a large quantity of a chiral target molecule. Over the last two decades, more than a half-dozen commercial industrial processes have been developed that use asymmetric catalysis as the key step in the production of enantiomerically pure compounds with a tremendous effort focused on developing new asymmetric catalysts for these reactions (Morrison J. D., ed. *Asymmetric Synthesis*, New York: Academic Press, 1985:5; Bosnich B., ed. *Asymmetric Catalysis*, Dordrecht, Netherlands: Martinus Nijhoff Publishers, 1986: Brunner H. *Synthesis*, 1988:645; Noyori R., Kitamura M., in Scheffold R., ed. *Modern Synthetic Methods*, Berlin Hedelberg: Springer-Verlag, 1989;5: 115; Nugent W. A., RajanBabu T. V., Burk M. J. *Science*, 1993;259:479; Ojima I., ed. *Catalytic Asymmetric Synthesis*, New York: VCH, 1993; Noyori R. *Asymmetric Catalysis In Organic Synthesis*, New York: John Wiley & Sons, Inc, 1994).

Chiral phosphine ligands have played a significant role in the development of novel transition metal catalyzed asymmetric reactions to produce enantiomeric excess of compounds with desired activities. The first successful attempts at asymmetric hydrogenation of enamide substrates were accomplished in the late 1970s using chiral bisphosphines as transition metal ligands (Vineyard B. D., Knowles W. S., Sabacky M. J., Bachman G. L., Weinkauff D. J. *J. Am. Chem. Soc.* 1977;99(18):5946–52; Knowles W. S., Sabacky M. J., Vineyard B. D., Weinkauff D. J. *J. Am. Chem. Soc.* 1975;97(9):2567–8).

Since these first published reports, there has been an explosion of research geared toward the synthesis of new chiral bisphosphine ligands for asymmetric hydrogenations and other chiral catalytic transformations (Ojima I., ed. *Catalytic Asymmetric Synthesis*, New York: VCH Publishers, Inc, 1993; Ager D. J., ed. *Handbook of Chiral Chemicals*, Marcel Dekker, Inc, 1999). Highly selective rigid chiral phospholane ligands have been used to facilitate these asymmetric reactions. For example, phospholane ligands are used in the asymmetric hydrogenation of enamide substrates and other chiral catalytic transformations.

BPE, Duphos, and BisP ligands are some of the most efficient and broadly useful ligands developed for asymmetric hydrogenation to date (Burk M. J. *Chemtracts* 1998;11 (11):787–802 (CODEN: CHEMFW ISSN:1431–9268. CAN 130:38423; AN 1998:698087 CAPLUS); Burk M. J., Bienewald F., Harris M., Zanotti-Gerosa A. *Angew Chem., Int.* Ed. 1998;37(13/14): 1931–1933; Burk, M. J., Casy G., Johnson N. B. *J. Org. Chem.* 1998;63(18):6084–6085; Burk M. J., Kalberg C. S., Pizzano A. *J. Am. Chem. Soc.* 1998;120 (18):4345–4353; Burk M. J., Harper T., Gregory P., Kalberg C. S. *J. Am. Chem. Soc.* 1995;117(15):4423–4424; Burk M. J., Feaster J. E., Nugent W. A., Harlow R. L. *J. Am. Chem. Soc.* 1993;115(22):10125–10138; Nugent W. A., RajanBabu T. V., Burk M. J. *Science* (Washington, D.C. 1883-) 1993;259(5094):479–483; Burk M. J., Feaster J. E., Harlow R. L. *Tetrahedron: Asymmetry* 1991;2(7):569–592; Burk M J. *J. Am. Chem. Soc.* 1991;113(22):8518–8519; Imamoto T., Watanabe J., Wada Y., Masuda H., Yamada H., Tsuruta H. et al. *J. Am. Chem. Soc.* 1998;120(7):1635–1636; Zhu G, Cao P, Jiang Q, Zhang X. *J. Am. Chem. Soc.* 1997;119(7):1799–1800). For example, a Rhodium/Duphos complex can be used to selectively form (S)-(+)-3-(aminomethyl)-5-methylhexanoic acid, known as pregabalin, which is used as an anti-seizure drug. The S-enantiomer, which is produced in enantiomeric excess, is preferred because it shows better anticonvulsant activity than the R-enantiomer (Yuen et al., *Bioorganic & Medicinal Chemistry Letters* 1994;4:823).

The success of BPE, DuPhos, and BisP transition metal complexes in asymmetric hydrogenations is derived from many factors. For example, substrate to catalyst ratios of up to 50,000/1 have been demonstrated. Also, high rates of substrate conversion to product using low hydrogen pressures have been observed with catalysts made from these ligands.

BPE, Duphos, and BisP have shown high enantioselectivities in numerous asymmetric reactions. Improved reaction of BPE, Duphos, and BisP is attributed to, among other factors, rigidity in their $C_2$-symmetric structure. If the spatial area of a metal/phosphine ligand structure, such as BisP, is divided into four quadrants, as shown in FIG. 1, alternating hindered and unhindered quadrants are formed. This structural feature creates areas of hindrance in the BisP/metal complexes and produces desired stereochemical results in asymmetric hydrogenation reactions. However, there are a variety of reactions in which only modest enantioselectivity has been achieved with these ligands. While high selectivity has been observed in many reactions using these chiral diphosphine ligands, there are many reactions where these ligands are not very efficient in terms of activity and selectivity. Further, there are many disadvantages associated with these ligands, which limits their application.

For example, multiple chiral centers in these ligands increases the difficulty in synthesis of these compounds. Further, the multiple chiral centers could increase the cost associated with forming the ligands.

High enantioselectivities have been observed in asymmetric hydrogenation for a narrow range of substrates, such as enamides, enol esters, and succinates. Many of these successful results have been obtained using optically pure $C_2$-symmetric rhodium-phosphine complexes as hydrogenation catalysts. Therefore, $C_2$-symmetry has become a popular characteristic in the design of chiral ligands that are used to make these complexes. Unique to the substrates for which asymmetric hydrogenation has been successful is an olefin and a carbonyl group which are separated by one atom. During asymmetric hydrogenation, the olefin and the carbonyl bind to the metal center in a well-defined conformation. This is thought to be of consequence in an asymmetric hydrogenation.

$C_2$-symmetric bisphosphines, such as BisP, have been synthesized and used in asymmetric catalysis, as shown in FIG. 2 (Imamoto, T., Watanabe J., Wada Y., Masuda H., Yamada H., Tsuruta H., Matsukawa S., Yamaguchi K. *J. Am. Chem. Soc.* 1998;120(7):1635–1636). A proton from one of the methyl groups of tert-butyldimethyl phosphine is selectively deprotonated with a chiral base, such as s-BuLi and (−)-sparteine, and then the resulting anion couples with itself in the presence of copper(II) chloride to provide the bisphosphine borane protected ligand, in about 40% yield and >99% enantiomeric excess after recrystallization. The rhodium complex of BisP is known to give high enantiomeric excess in hydrogenation reactions for a variety of substrates. For instance, the rhodium-BisP catalyst hydrogenates α-N-acetylmethylacrylate to produce 98% enantiomeric excess (Imamoto T. et al., supra, 1998).

A drawback to the synthesis of the BisP ligand in FIG. 2 is that only one antipode of sparteine is available in nature, and therefore, only one enantiomer of the ligand (the S,S isomer) can be synthesized via this route.

Basic research has been done by a variety of groups in the late 1970s on the mechanism and origin of enantioselectivity of asymmetric hydrogenation reactions which result in high enantiomeric excess (Alcock N. W., Brown J. M.; Derome A. E., Lucy A. R. *J. Chem. Soc. Chem. Comm.* 1985:575; Brown J. M., Chaloner P. A., Morris G. A. *J. Chem. Soc. Chem. Comm.* 1983:664; Halpern J. *Science* 1982;217,401; Brown J. M., Chaloner P. A. *J. Chem. Soc. Chem. Comm.* 1980;344). The 3-dimensional structure of a $C_2$-symmetric complex like the rhodium complex of BisP has four quadrants that alternate hindered and unhindered, as shown in FIG. 1.

Ligand and metal/ligand complexes are needed that can further improve the production of enantiomerically active forms of compounds. Thus, there is a need to develop methods for the production of and to synthesize compounds that reduce the number of chiral centers on a molecule and through prohibitive substituents on the ligand improve enantioselectivity in asymmetric reactions.

SUMMARY OF THE INVENTION

The present invention provides for non-$C_2$-symmetric bisphosphine ligands. Non-$C_2$ bisphosphine ligands when complexed with a metal, serve as catalysts in asymmetric hydrogenation reactions to form enantiomerically enriched compounds.

Thus, one aspect of the present invention provides a non-$C_2$-symmetric bisphosphine ligand comprising an achiral phosphorus group, a chiral phosphorus group, and a bridge moiety that links the achiral and chiral phosphorus groups as represented by general Formula I:

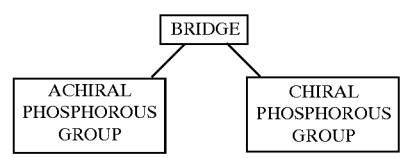

I wherein:

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and the bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

Another aspect of the present invention provides a non-$C_2$-symmetric bisphosphine compound represented by general Formula II:

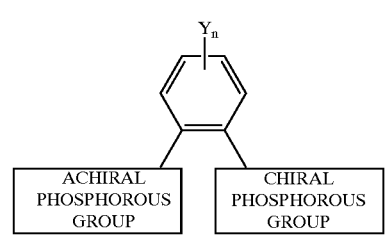

II wherein:

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and each Y is independently halogen, alkyl, alkoxy, aryl, aryloxy, nitro, amino, vinyl, substituted vinyl, alkynyl, or sulfino, and n is an integer from 0 to 4.

Another aspect of the present invention provides an atropisomeric ligand comprising a pair of backbone moieties A and B, which are linked together and individually bond to separate phosphorous groups as represented by Formula IIb.

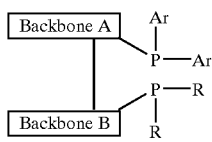

IIb

In Formula IIb,

A and B are the same or different and are chosen so that together they form a chiral center, each of A and B being an aryl or heteroaryl group comprised of ring atoms optionally having non-hydrogen substituents;

R is a substituent exhibiting steric hindrance at least as great as an isopropyl group; and Ar is an aryl group.

Another aspect of the invention is directed to a method for forming P-chiral bisphosphine ligands. Compounds used as synthons during synthesis of non-$C_2$-symmetric bisphosphine ligands include compounds represented by Formulas III, IV, V, and VI:

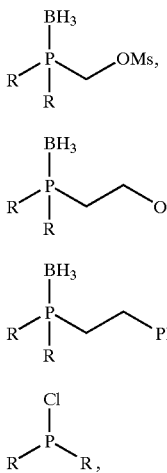

III

IV

V

VI wherein Ms is mesylate and R is a substituent exhibiting steric hindrance at least as great as an isopropyl group, and includes isopropyl, tert-butyl, 1,1,3,3-tetramethylbutyl, $C_{5-15}$-cycloalkyl, such as cyclopentyl and cyclohexyl; 1-methyl-cyclopentyl, 1-methyl-cyclohexyl, 1-ol-$C_{5-15}$-cycloalkyl, dialkylamino, diarylamino, 1-alkoxy-$C_{5-15}$-cycloalkyl, adamantyl, 1,1-dimethylpropyl, 1,1-diethylbutyl, and a bulky aryl group such as substituted phenyl.

Another aspect of the invention is directed to methods for forming non-$C_2$-bisphosphine ligands. The methods include preparing compounds of general structural Formulas I and II, as shown in FIG. 4–FIG. 12.

A further aspect of the present invention provides a non-$C_2$ symmetric bisphosphine ligand complex, the ligand comprising an achiral phosphorus group, a chiral phosphorus group, and a bridge moiety that links the achiral and chiral phosphorus groups. The complex is represented by general Formula VIII:

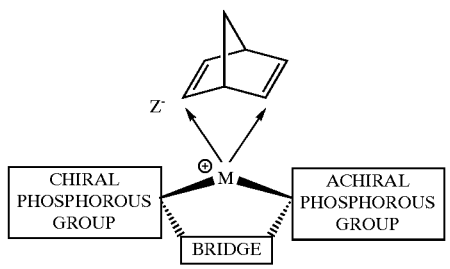

VIII wherein:

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent;

the Bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

M is a transition metal, an actinide, or a lanthanide; and Z is $BF_4$, $PF_6$, $SbF_6$, OTf, or $ClO_4$.

Yet another aspect of the invention is directed to forming enantiomeric excesses of compounds catalyzed with the metal/non-$C_2$-symmetric bisphosphine complexes in asymmetric reactions.

DETAILED DESCRIPTION OF THE INVENTION

Figure 1:
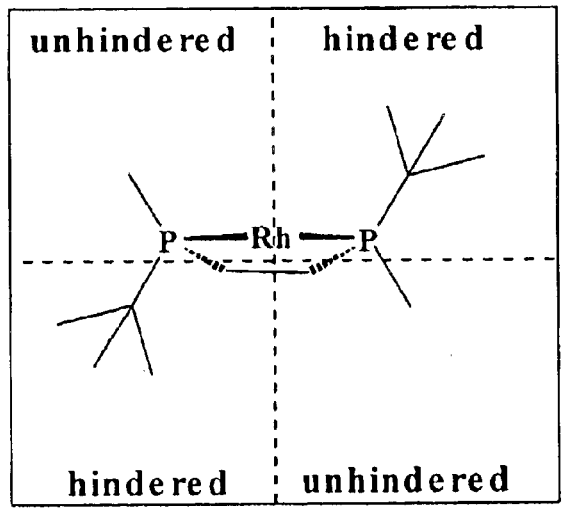
FIG. 1 depicts a spatial arrangement of a metal/phosphine ligand.
Figure 2:
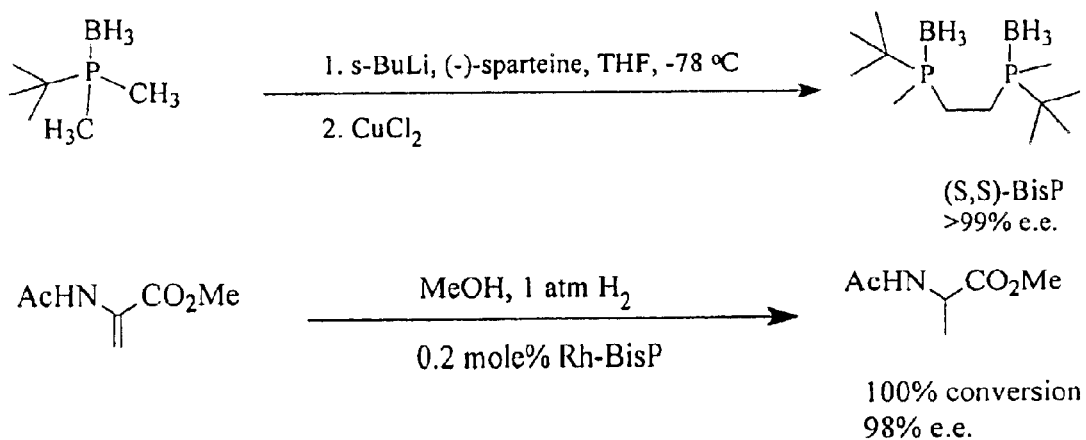
FIG. 2 shows representative schemes for preparing $C_2$-symmetric bisphosphines, such as BisP, and for using $C_2$-symmetric bisphosphines in asymmetric catalysis.

The present invention is applicable to the synthesis of non-$C_2$-symmetric bisphosphine ligands for use in metal/non-$C_2$-symmetric bisphosphine complexes for asymmetric catalysis. In particular, the present invention is directed to reacting the metal/non-$C_2$-symmetric bisphosphine complexes to produce enantiomeric excesses of a compound in asymmetric hydrogenation syntheses. While the present invention is not so limited, an appreciation of various aspects of the invention will be gained through a discussion of the examples provided below.

Definitions

The term "substituted," as used in this disclosure, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The term "alkyl", as used in this disclosure, includes a straight or branched saturated aliphatic hydrocarbon chain, such as, for example, methyl, ethyl, propyl, isopropyl (1-methylethyl), butyl, tert-butyl (1,1-dimethylethyl), and the like.

The term "aryl" group, as used in this disclosure, includes an aromatic hydrocarbon group, including fused aromatic rings, such as, for example phenyl and naphthyl. Such groups may be unsubstituted or substituted on the aromatic ring by, for example, an alkoxy group of 1 to 4 carbon atoms, an amino group, a hydroxy group, or an acetyloxy group.

The term "aralkyl" group, as used in this disclosure, includes an aromatic hydrocarbon group, including fused aromatic rings, such as for example, phenyl and naphthyl, bonded to an alkyl group with the alkyl bonded to the phospholane ring. The aromatic hydrocarbon group may be unsubstituted or substituted (ring substituted aralkyl) by, for example, an alkoxy group of 1 to 4 carbon atoms, an amino group, a hydroxy group, or an acetyloxy group.

The term "heteroaryl" group, as used in this disclosure, includes an aromatic hydrocarbon group, including fused aromatic rings, such as, for example phenyl and naphthyl, in which one or more of the ring carbon atoms is substituted with nitrogen, oxygen or sulfur. Such groups may be unsubstituted or substituted on the aromatic ring by, for example, an alkoxy group of 1 to 4 carbon atoms, an amino group, a hydroxy group, or an acetyloxy group.

The term "LAH," as used in this application, is defined as lithium aluminum hydride.

Unless otherwise indicated, the abbreviations and acronyms used in this specification conform to the list of standard abbreviations and acronyms published in the J. Org. Chem., 67(1): A24 (2002).

For the purpose of this disclosure, the "corresponding enantiomer" means that if a compound includes a stereochemical configuration designated as R, the corresponding enantiomer is the S configuration. If a compound has an S configuration, the corresponding enantiomer is the R configuration. If a compound has a stereochemical configuration of 1R,2S, the "corresponding enantiomer" is the 1S,2R compound. Similarly, if a compound has a 1S,2R configuration, the "corresponding enantiomer" is the 1R,2S compound. If a P-chiral compound has a 1S,2S configuration, the "corresponding enantiomer" is the 1R,2R compound. If a compound has a 1R,2R configuration, the "corresponding enantiomer" is the 1S,2S compound, and so on For the purpose of this disclosure, a high level of enantioselectivity means that a given reaction (e.g., hydrogenation) yields a product of greater than or equal to about 80%, and preferably, greater than or equal to about 90% enantiomeric excess (abbreviated e.e.).

Enantiomeric excess is defined as the ratio (%R−%S)/(%R+%S)×100, where %R is the percentage of R enantiomer and %S is the percentage of S enantiomer in a sample of optically active compound. For the purpose of this disclosure, by a "compound with a high degree of enantiomeric purity," or a "compound of high enantiomeric purity" is meant a compound that exhibits enantiomeric excess to the extent of greater than or equal to about 90%, preferably, greater than or equal to about 95% enantiomeric excess (abbreviated e.e.).

Non-$C_2$-Symmetric Bisphosphines

The present invention provides novel non-$C_2$ symmetric bisphosphine substituted compounds, which are comprised of an achiral phosphorus group, a chiral phosphorus group, and a bridge moiety that links the achiral and chiral phosphorous groups. The compounds have general Formula I.

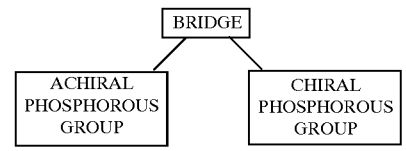

I wherein:
the achiral phosphorous group includes at least one achiral phosphorous atom having one bond to each of two identical atoms other than the bridge;
the chiral phosphorous group comprises at least one phosphorous atom, wherein the at least one phosphorous atom is chiral or the at least one phosphorous atom is bonded to a chiral substituent; and
the bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

Another non-$C_2$-symmetric bisphosphine compound of present invention has the general Formula II:

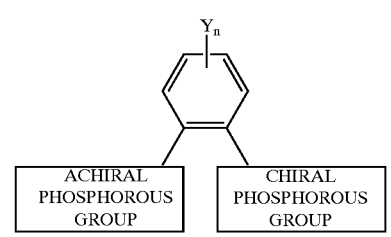

II wherein:
the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and each Y is independently halogen, alkyl, alkoxy, aryl, aryloxy, nitro, amino, vinyl, substituted vinyl, alkynyl, or sulfino, and n is an integer from 0 to 4.

Achiral phosphorous groups include, but are not limited to, the following:

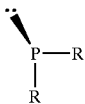

wherein R is a substituent exhibiting steric hindrance at least as great as an isopropyl group, and includes isopropyl, tert-butyl, 1,1,3,3-tetramethylbutyl, $C_{5-15}$-cycloalkyl, such as cyclopentyl and cyclohexyl, 1-methyl-cyclopentyl, 1-methyl-cyclohexyl, 1-ol-$C_{5-15}$-cycloalkyl, dialkylamino, diarylamino, 1-alkoxy-$C_{5-15}$-cycloalkyl, adamantyl, 1,1-dimethylpropyl, 1,1-diethylbutyl, and a bulky aryl group such as substituted phenyl.

Chiral phosphorous groups include, but are not limited to, the following and their corresponding enantiomers:

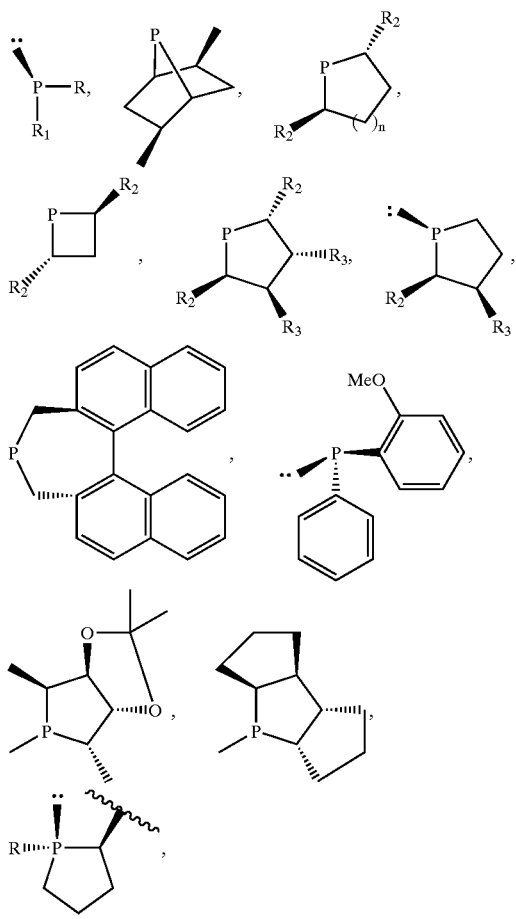

wherein:
R is a substituent exhibiting steric hindrance at least as great as an isopropyl group, and includes isopropyl, tert-butyl, 1,1,3,3-tetramethylbutyl, $C_{5-15}$-cycloalkyl, such as cyclopentyl and cyclohexyl; 1-methyl-cyclopentyl, 1-methyl-cyclohexyl, 1-ol-$C_{5-15}$-cycloalkyl, dialkylamino, diarylamino, 1-alkoxy-$C_{5-15}$-cycloalkyl, adamantyl, 1,1-dimethylpropyl, 1,1-diethylbutyl, and a bulky aryl group such as substituted phenyl;

$R_1$ is hydrogen, methyl, straight chain alkyl or substituted alky of up to twenty carbon atoms, alkoxy or substituted alkoxy of up to twenty carbon atoms, monoalkylamino, or mono-arylamino, provided that $R_1$ and R are different;

$R_2$ is methyl, ethyl, isopropyl, cyclohexyl, hydroxy, alkoxy, benzyl, a ring substituted benzyl, an aryl, or a ring substituted aryl;

$R_3$ is OBn, hydroxy, alkoxy, sulphonate, or hydrogen; and n is an integer between one and ten, inclusive.

A preferred R group for the achiral phosphorous groups of compounds of general Formula I is tert-butyl. Examples of other preferred non-$C_2$-symmetric bisphosphine ligands of general Formula I include, but are not limited to, those compounds in which R is isopropyl, adamantyl, (1,1-dimethylpropane), (1,1-diethylbutane), cyclopentyl, or cyclohexyl, and their corresponding enantiomers.

The non-$C_2$-symmetric bisphosphine substituted compound, 1-(di-tert-butyl-phosphanyl)-((R)-2-tert-butyl-methyl-phosphanyl) ethane is represented by the Formula Ia:

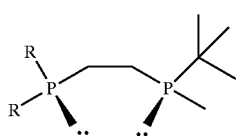

wherein R is tert-butyl.

The non-$C_2$-symmetric bisphosphine substituted compound, 1-((S)-2,2'-phosphanyl-1,1'-binaphthyl)-2-((R)-2-tert-butyl-methyl-phosphanyl) ethane is represented by the Formula Ib:

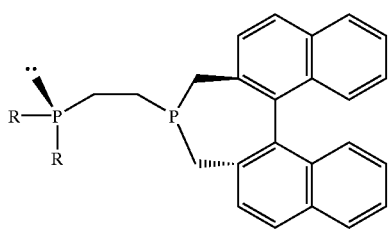

wherein R is tert-butyl.

The non-$C_2$-symmetric bisphosphine substituted compound, 1-((R)-2-tert-butyl-methyl-phosphanyl )-2-((R,R)-2,5-dialkylphosphanyl) ethane is represented by the Formula Ic:

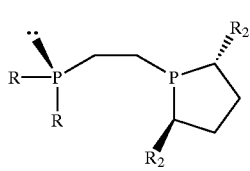

wherein R is tert-butyl, and $R_2$ is alkyl.

The non-$C_2$-symmetric bisphosphine substituted compound, 1-((R)-2-tert-butyl-methyl-phosphanyl)-2-((R, R)-2,5-dialkylphosphanyl) benzene is represented by the Formula IIa:

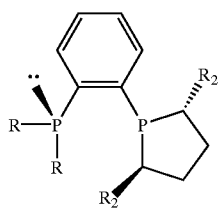

IIa wherein R is tert-butyl, and R$_2$ is alkyl.

Compounds of general Formulas Ia, Ib, Ic, and IIa include the corresponding enantiomer of the compound shown in the structural formulas. Additionally, R is generally any substituent exhibiting steric hindrance at least as great as an isopropyl group, and in addition to isopropyl and tert-butyl, includes 1,1,3,3-tetramethylbutyl, C$_{5-15}$-cycloalkyl, such as cyclopentyl and cyclohexyl, 1-methyl-cyclopentyl, 1-methyl-cyclohexyl, 1-ol-C$_{5-15}$-cycloalkyl, dialkylamino, diarylamino, 1-alkoxy-C$_{5-15}$-cycloalkyl, adamantyl, 1,1-dimethylpropyl, 1,1-diethylbutyl, and a bulky aryl group such as substituted phenyl. Besides alky, R$_2$ can be cyclohexyl, hydroxy, alkoxy, benzyl, a ring substituted benzyl, an aryl, or a ring substituted aryl.

The bisphosphine compounds of Formula I and II are useful as transition metal ligands in asymmetric catalysis. The use of these ligands to form transition metal catalysts results in a high level of enantioselective and stereochemical control in the catalyzed hydrogenation of unsaturated substrates.

Compounds I and II include one to three chiral centers instead of the four chiral centers that are found in molecules such as Duphos. Ligands displaying the structural motif of Ia do not necessarily have to contain bulky groups on phosphorous that are the same. In other words, as long as there are three sterically hindered quadrants in the metal-ligand complex, the desired effect in asymmetric transformations will be achieved.

Certain atropisomeric ligands also exhibit three sterically hindered quadrants when complexed with a metal, and therefore may be used to catalyze asymmetric transformations. These ligands comprise a pair of rigid backbone moieties A and B, which are linked together and individually bond to separate phosphorous groups as represented by Formula IIb

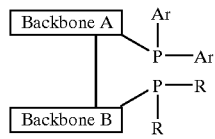

IIb wherein:
  backbone A and backbone B are the same or different and are chosen so that together they form a chiral center, each of the backbones being an aryl or heteroaryl group comprised of ring atoms optionally having non-hydrogen substituents;
  R is a substituent exhibiting steric hindrance at least as great as an isopropyl group, and includes isopropyl, tert-butyl, 1,1,3,3-tetramethylbutyl, C$_{5-15}$-cycloalkyl, such as cyclopentyl and cyclohexyl; 1-methyl-cyclopentyl, 1-methyl-cyclohexyl, 1-ol-C$_{5-15}$-cycloalkyl, dialkylamino, diarylamino, 1-alkoxy-C$_{5-15}$-cycloalkyl, adamantyl, 1,1-dimethylpropyl, 1,1-diethylbutyl, and a bulky aryl group such as substituted phenyl; and Ar is an aryl group.

The disclosed atropisomeric ligands fit the "three hindered quadrant" motif because the R substituents are bulky groups, which block two quadrants. While the two aryl groups are separately not necessarily bulky, the chirality of the biaryl or biheteroaryl backbones orients the two aryl groups such that they lie in planes that are approximately orthogonal to one another, thus blocking one quadrant and leaving the other quadrant unhindered.

As noted above, backbone A and backbone B can be any aryl or heteroaryl group, provided that they form a chiral center. Particularly advantageous backbones include phenyl or naphthyl groups, which yield the following 2,2'-bisphosphinebiaryl ligands:

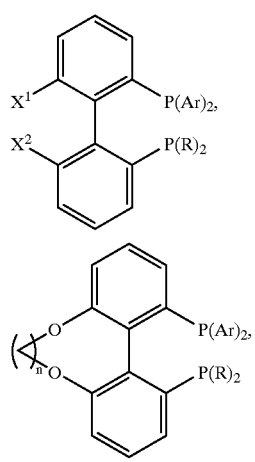

in which n is an integer between 1 and 10, inclusive, and

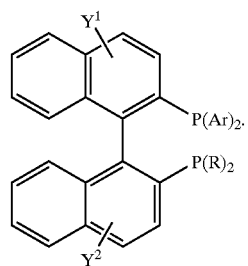

For each of the 2,2'-bisphosphinebiaryl ligands depicted above, Ar and R are the same as defined above for Formula IIb, and X$^1$, X$^2$, Y$^1$ and Y$^2$ are independently any substituents that make the ligand chiral. One of X$^1$ and X$^2$ may be hydrogen as long as the other substituent is bulky (i.e., provides steric hindrance at least as great as isopropyl). Useful X$^1$, X$^2$, Y$^1$ and Y$^2$ include halogen, alkyl (e.g., tert-butyl), alkoxy, aryl, aryloxy, nitro, amino, vinyl, substituted vinyl, alkynyl, or sulfino.

Several intermediate synthon compounds can be used to form non-C$_2$-symmetric compounds, such as those with the general Formula I. Useful synthons includes those provided in Formulas III, IV, V, and VI:

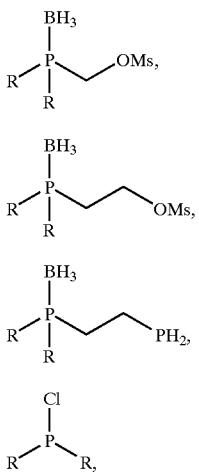

wherein Ms is mesylate, and R is a substituent exhibiting steric hindrance at least as great as an isopropyl group, and includes isopropyl, tert-butyl, 1,1,3,3-tetramethylbutyl, $C_{5-15}$-cycloalkyl, such as cyclopentyl and cyclohexyl; 1-methyl-cyclopentyl, 1-methyl-cyclohexyl, 1-ol-$C_{5-15}$-cycloalkyl, dialkylamino, diarylamino, 1-alkoxy-$C_{5-15}$-cycloalkyl, adamantyl, 1,1-dimethylpropyl, 1,1-diethylbutyl, and a bulky aryl group such as substituted phenyl.

The above bisphospholane compounds of Formulas I, II, and their corresponding enantiomers can be complexed with any of the transition metals as well as the lanthanides and actinides. Such complexes are formed by methods known in the art.

An additional non-$C_2$ symmetric bisphosphine ligand complex, includes a ligand comprised of an achiral phosphorus group, a chiral phosphorus group, and a bridge moiety that links the achiral and chiral phosphorus groups. The complex is represented by general Formula VIII and includes its corresponding enantiomer:

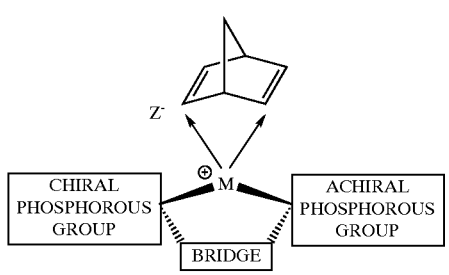

VIII wherein:
  the achiral phosphorous group includes at least one achiral phosphorous atom having one bond to each of two identical atoms other than the bridge;
  the chiral phosphorous group comprises at least one phosphorous atom, wherein the at least one phosphorous atom is chiral or the at least one phosphorous atom is bonded to a chiral substituent;
  the Bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

M is a transition metal, an actinide, or a lanthanide; and Z is $BF_4$, $PF_6$, $SbF_6$, OTf, or $ClO_4$.

Preferred transition metal complexes of the present invention are those including the above-described preferred compounds complexed with rhodium.

Synthesis of non-$C_2$ Bisphosphines

Figure 3:
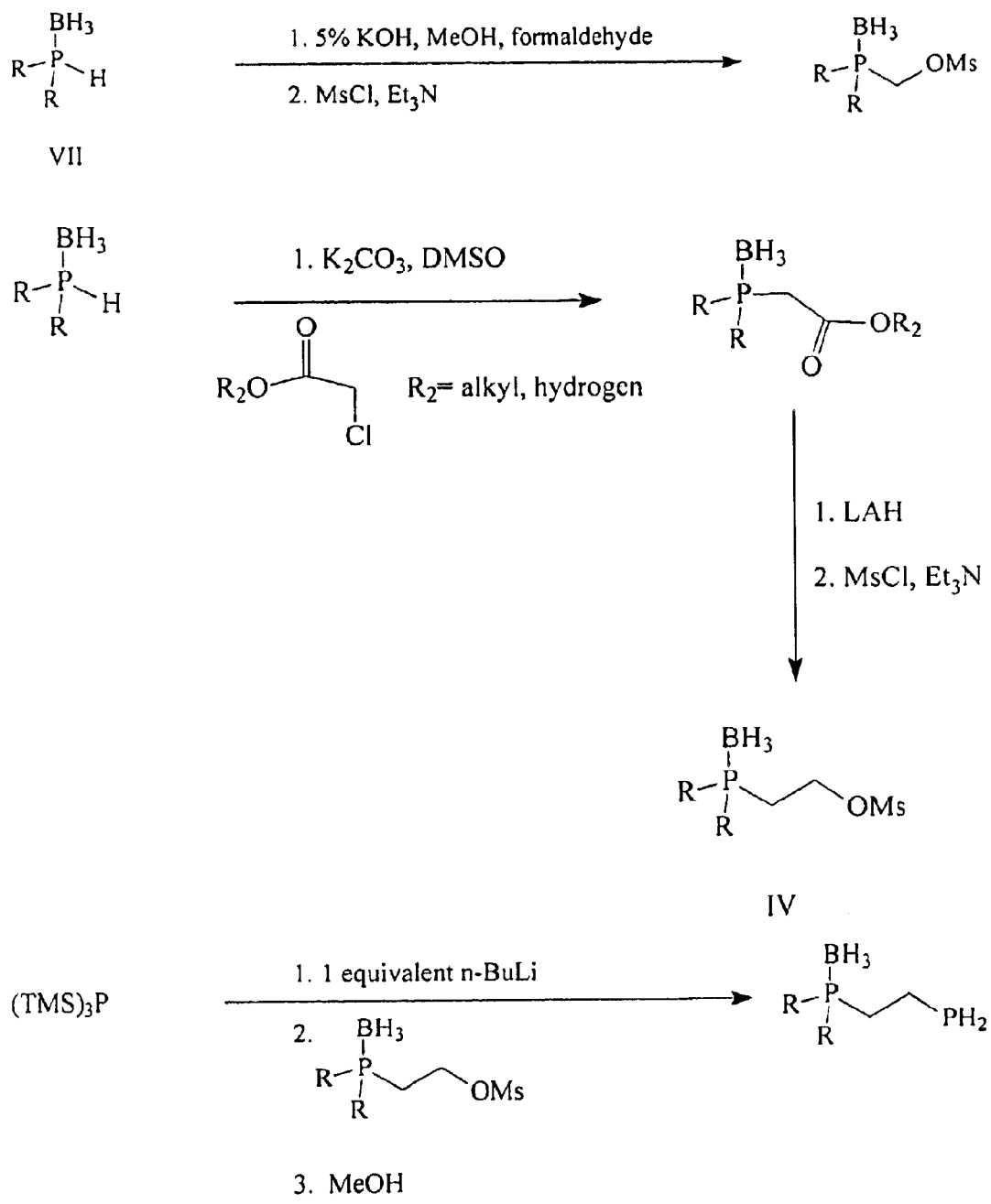
FIG. 3 shows schemes for preparing synthons that can be used to prepare non-$C_2$-symmetric borane-protected ligands.
Figure 4:
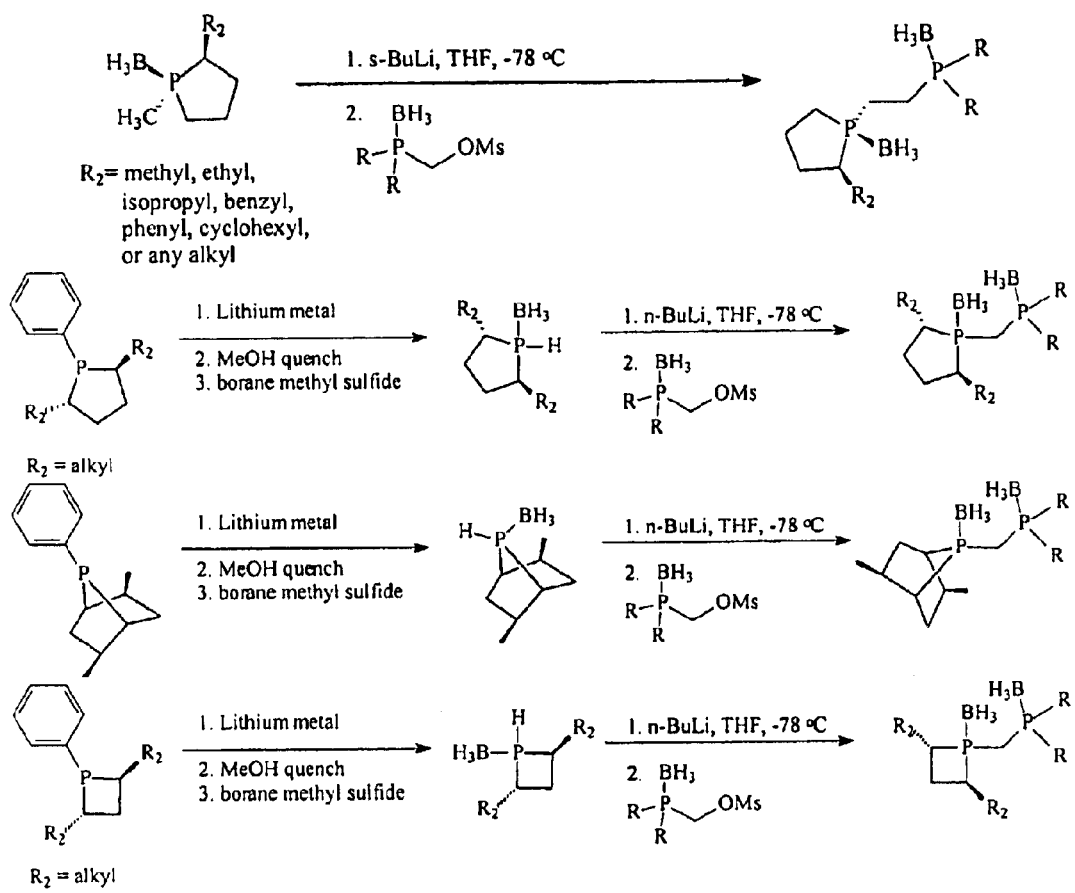
FIG. 4 shows schemes for preparing non-C2-symmetric ligands using synthon III.
Figure 5:
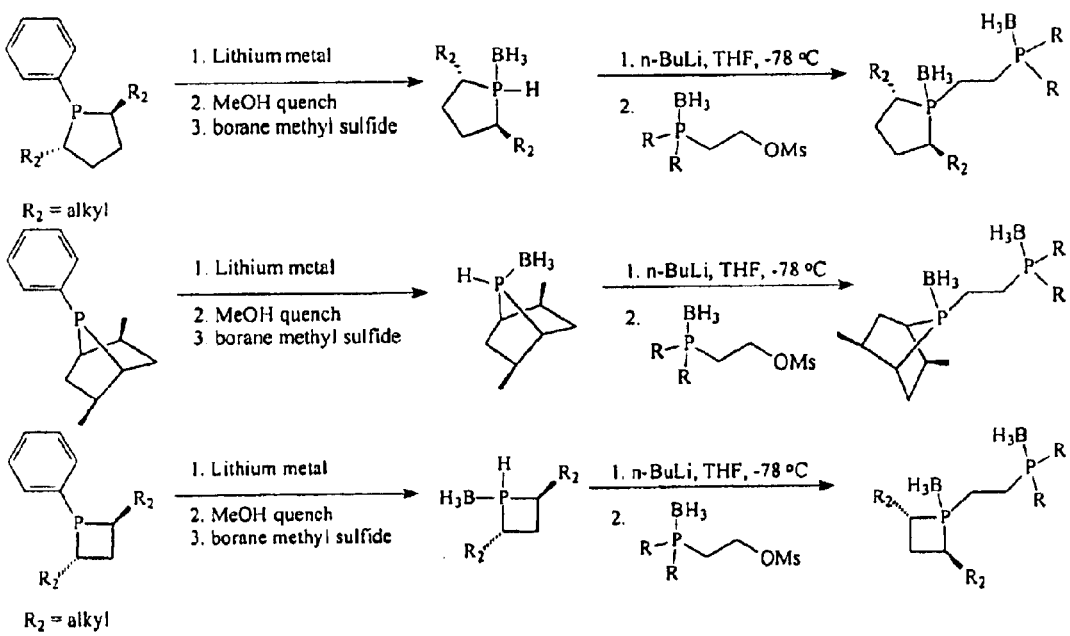
FIG. 5 shows schemes for preparing non-C2-symmetric ligands using synthon IV.
Figure 6:
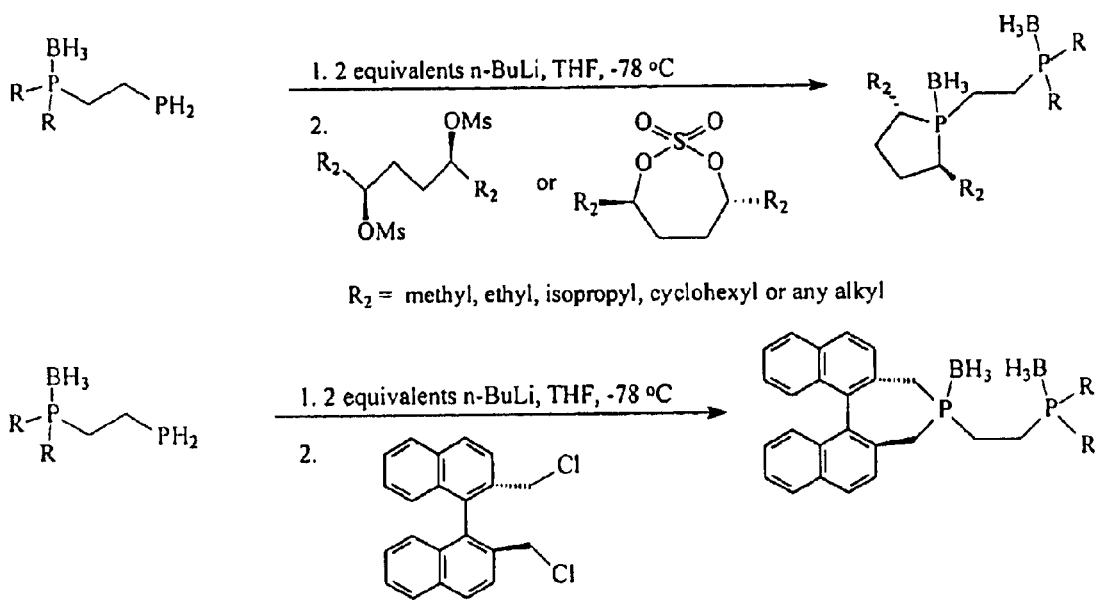
FIG. 6 shows schemes for preparing non-C2-symmetric ligands using synthon V.
Figure 7:
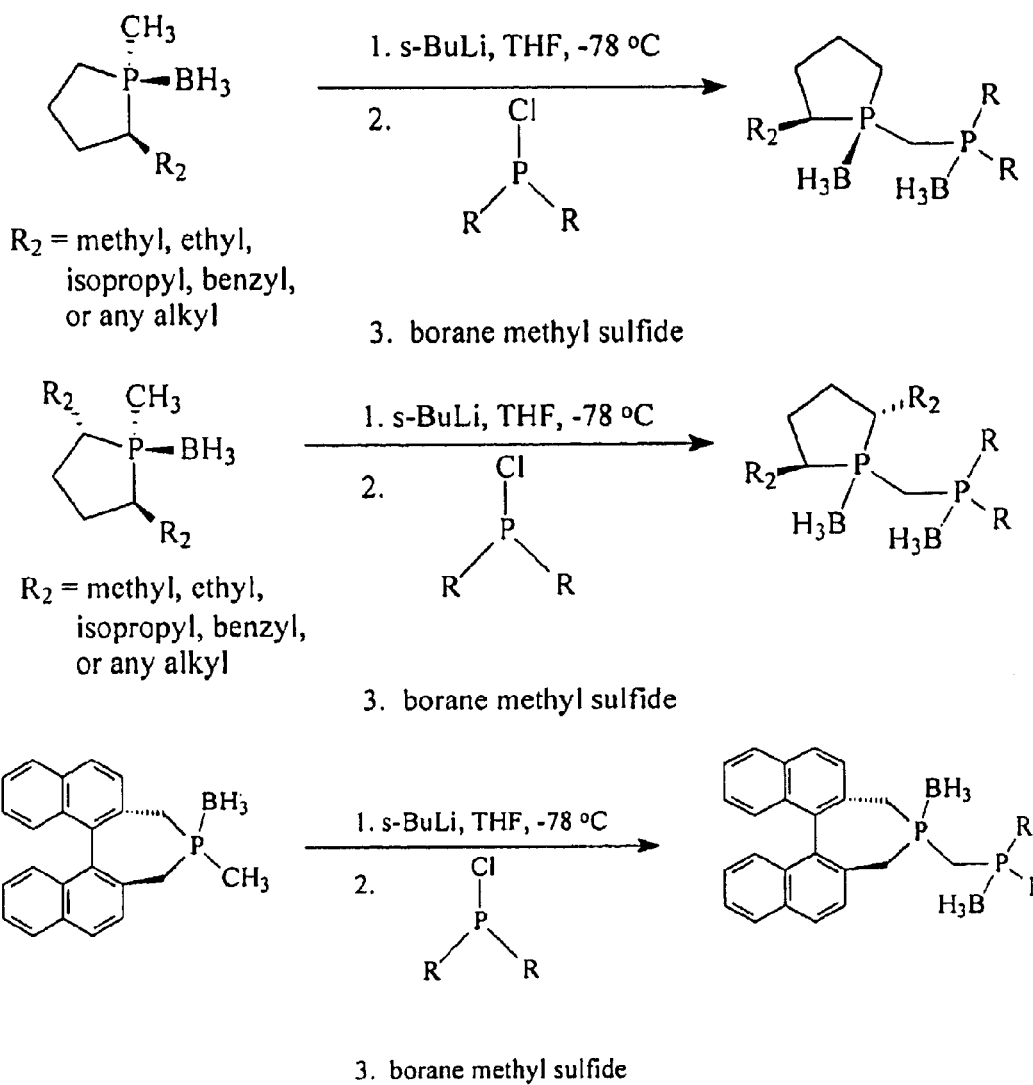
FIG. 7 shows schemes for preparing non-C2-symmetric ligands using synthon VI.
Figure 8:
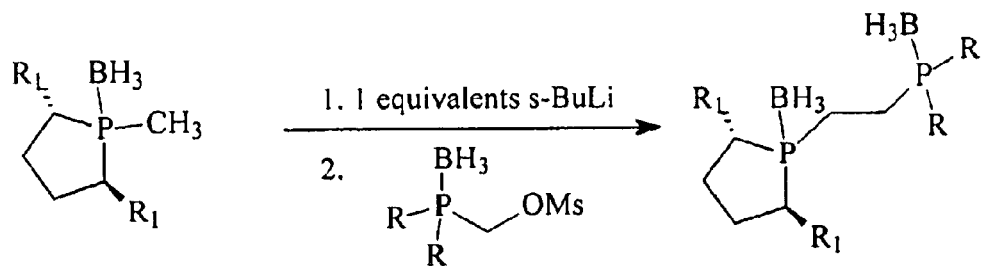
FIG. 8 shows a scheme for preparing non-C2-symmetric ligands using synthon VII.

The synthesis the non-$C_2$ borane-protected ligands can be formed through synthons that are prepared as shown in FIG. 3. For the synthons shown, Ms is mesylate and R is generally any bulky group as described above for the achiral phosphorus groups. In particular, R is tert-butyl, isopropyl, adamantyl, (1,1)-dimethylpropane, (1,1-diethylbutane), cyclopentyl or cyclohexyl.

An additional synthon is a compound with the formula:

VI wherein R is generally any bulky group as described above for the achiral phosphorus groups, and is advantageously tert-butyl, isopropyl, adamantyl, (1,1)-dimethylpropane, (1,1-diethylbutane), cyclopentyl or cyclohexyl. The above synthons can be used in a variety of reactions to form non-$C_2$-symmetric ligands as shown in FIG. 4–FIG. 8. In each of the schemes shown in FIG. 4–FIG. 8, Ms is mesylate and R is generally any bulky group as described above for the achiral phosphorus groups. Particularly useful R substituents include tert-butyl, isopropyl, adamantyl, (1,1)-dimethylpropane, (1,1-diethylbutane), cyclopentyl or cyclohexyl.

Figure 9:
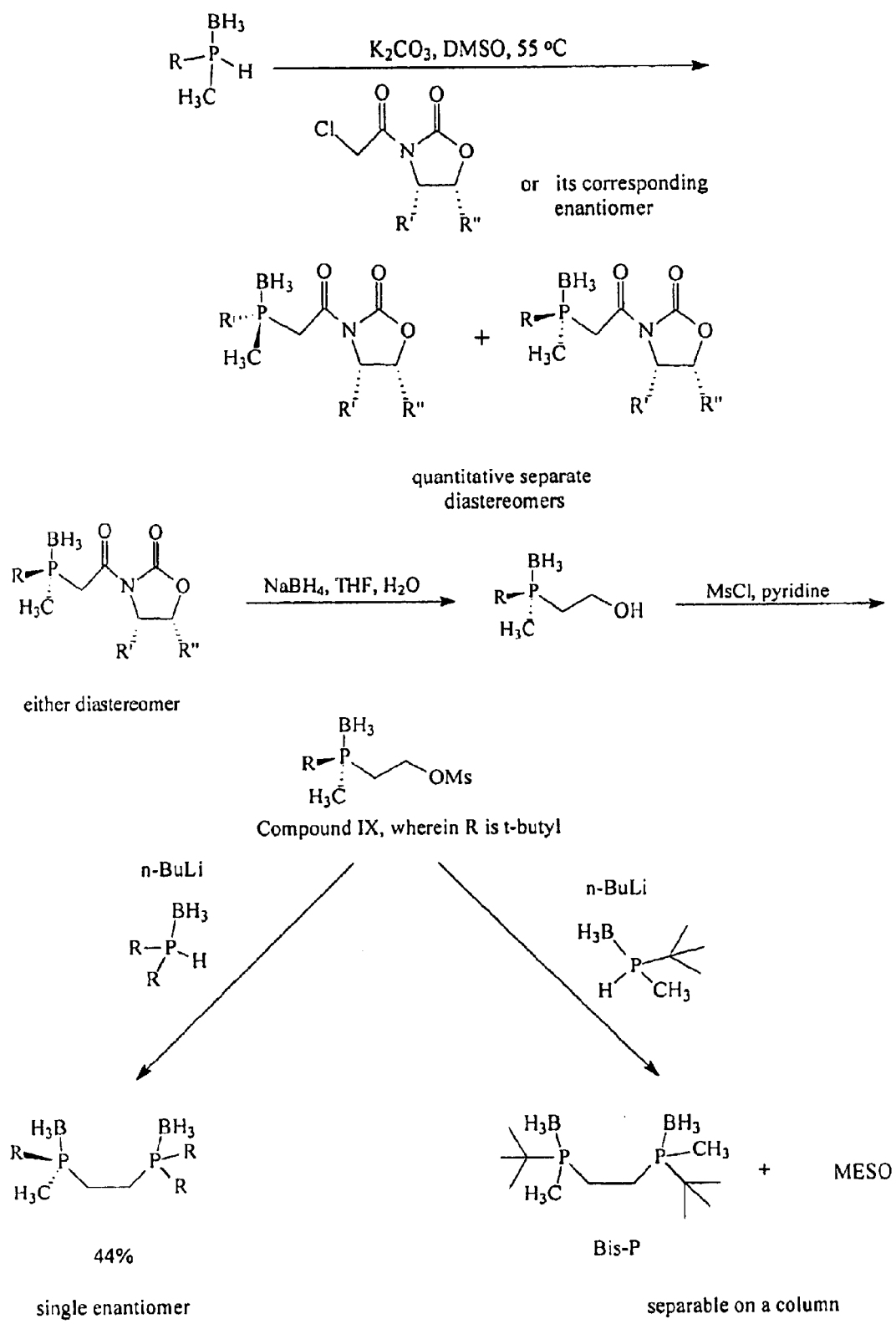
FIG. 9 shows a scheme for preparing compounds of Formula Ia.

FIG. 9 shows a method of synthesis to compound Ia. In the scheme shown in FIG. 9, Ms is mesylate and R is generally any bulky group as described above for the achiral phosphorus groups. Particularly useful R groups include tert-butyl, isopropyl, adamantyl, (1,1)-dimethylpropane, (1,1-diethylbutane), cyclopentyl or cyclohexyl; R' is methyl, benzyl, aryl, isopropyl; and R" is H, methyl, benzyl, aryl, and isopropyl.

The scheme shown in FIG. 9 includes reacting (+/−)-tert-butyl-methyl-phosphane borane as a starting material. This primary phosphine is made via a one-pot procedure starting from dichloromethylphosphine, reacting with dimethylsulfide-borane, tert-butyl magnesium chloride, and then LAH. (+/−)-tert-butyl-methyl-phosphane borane is reacted with a chiral auxiliary that includes $K_2CO_3$, DMSO, and N-chloroacetyl-(S)-(−)4-benzyl-2-oxazolidinone at 55° C. to form a mixture of diastereomers (S)-4-benzyl-3-[2-((R)-tert-butyl-methyl-phosphanyl)-ethanoyl]-oxazolidin-2-one and (S)-4-benzyl-3-[2-((S)-tert-butyl-methyl-phosphanyl)-ethanoyl]-oxazolidin-2-one in quantitive yield. These diastereomers can be separated either by column chromatography or via recrystallization.

Each diastereomer can then be reduced with $NaBH_4$ to remove the chiral auxiliary and form either enantiomer of the alcohol, 2-(tert-butyl-methyl-phosphanyl)-ethanol, as shown in FIG. 9. The alcohol is then reacted with mesylate chloride and pyridine to form the compound IX. The corresponding enantiomer of compound IX can also be formed by choosing the opposite diastereomer. Compound IX can then be reacted with a mixture of n-butyl lithium and compound VII. Alternatively, compound IX can then be reacted with a mixture of n-butyl lithium and tert-butylmethylphosphine borane to form Bis-P and a meso product.

Figure 10:
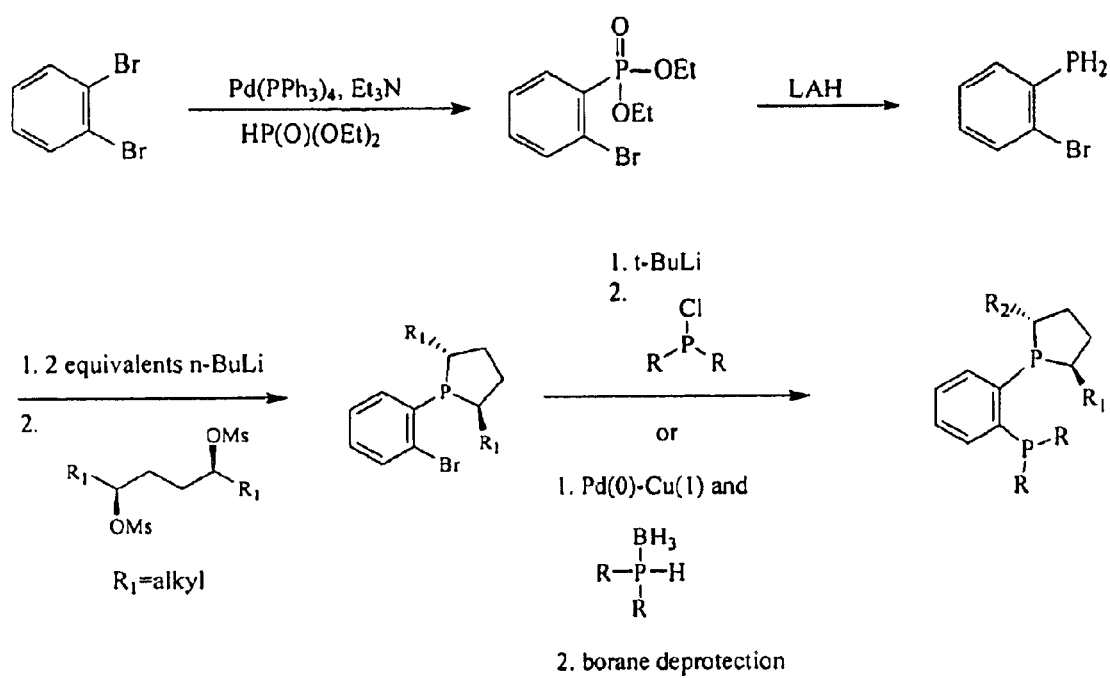
FIG. 10 shows a scheme for preparing compounds of Formula IIa.

The compound with the general Formula IIa can be synthesized via the route shown in FIG. 10, wherein Ms is mesylate and R is generally any bulky group as described above for the achiral phosphorus groups. Particularly useful R groups include tert-butyl, isopropyl, adamantyl, (1,1)-dimethylpropane, (1,1-diethylbutane), cyclopentyl or cyclohexyl.

Figure 11:
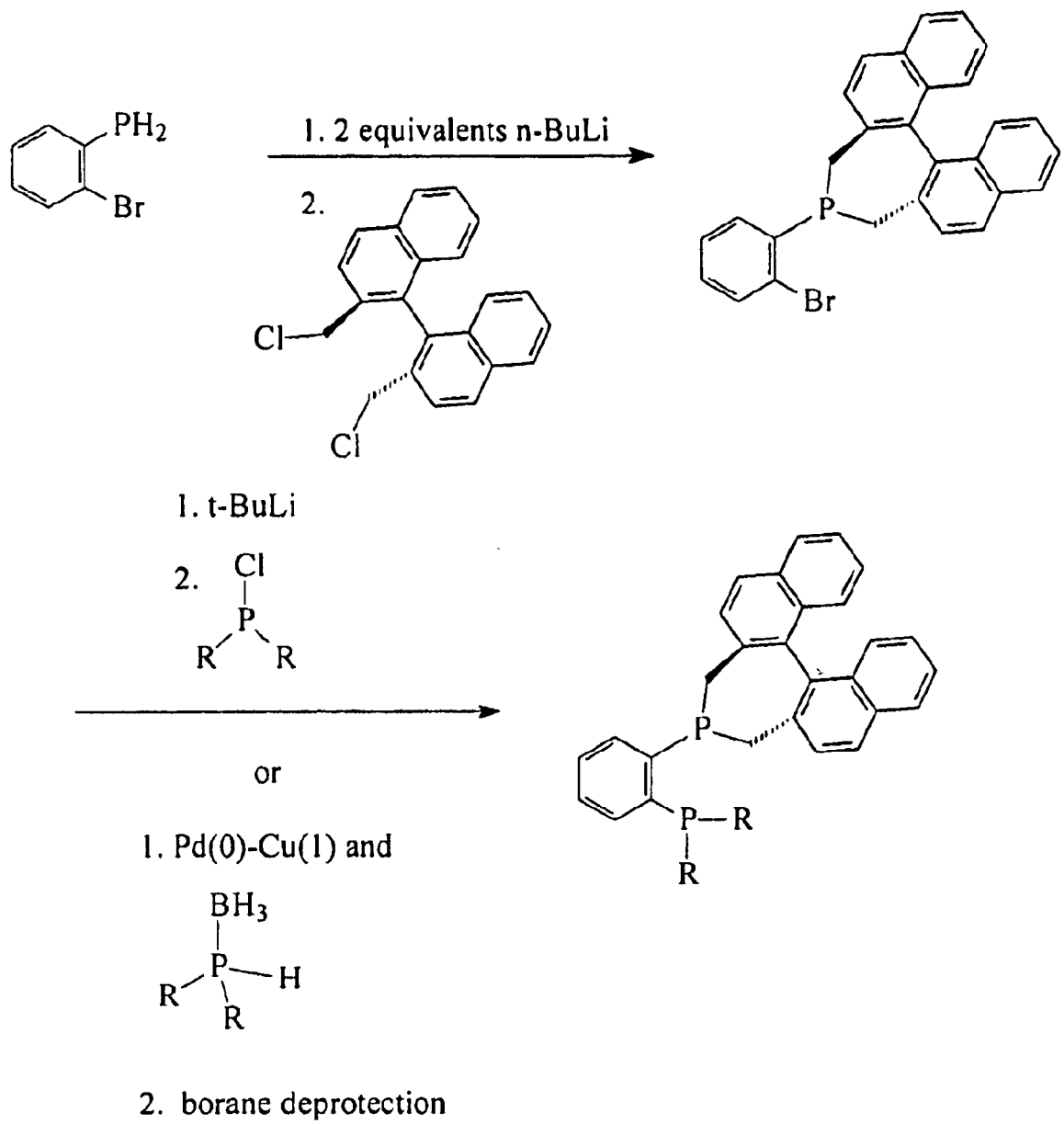
FIG. 11 shows a scheme for preparing compounds of Formula Ib.

The compound with the general Formula Ib can be synthesized via the route shown in FIG. 11, wherein R is generally any bulky group as described above for the achiral phosphorus groups, and is advantageously tert-butyl, isopropyl, adamantyl, (1,1)-dimethylpropane, (1,1-diethylbutane), cyclopentyl or cyclohexyl.

Figure 12:
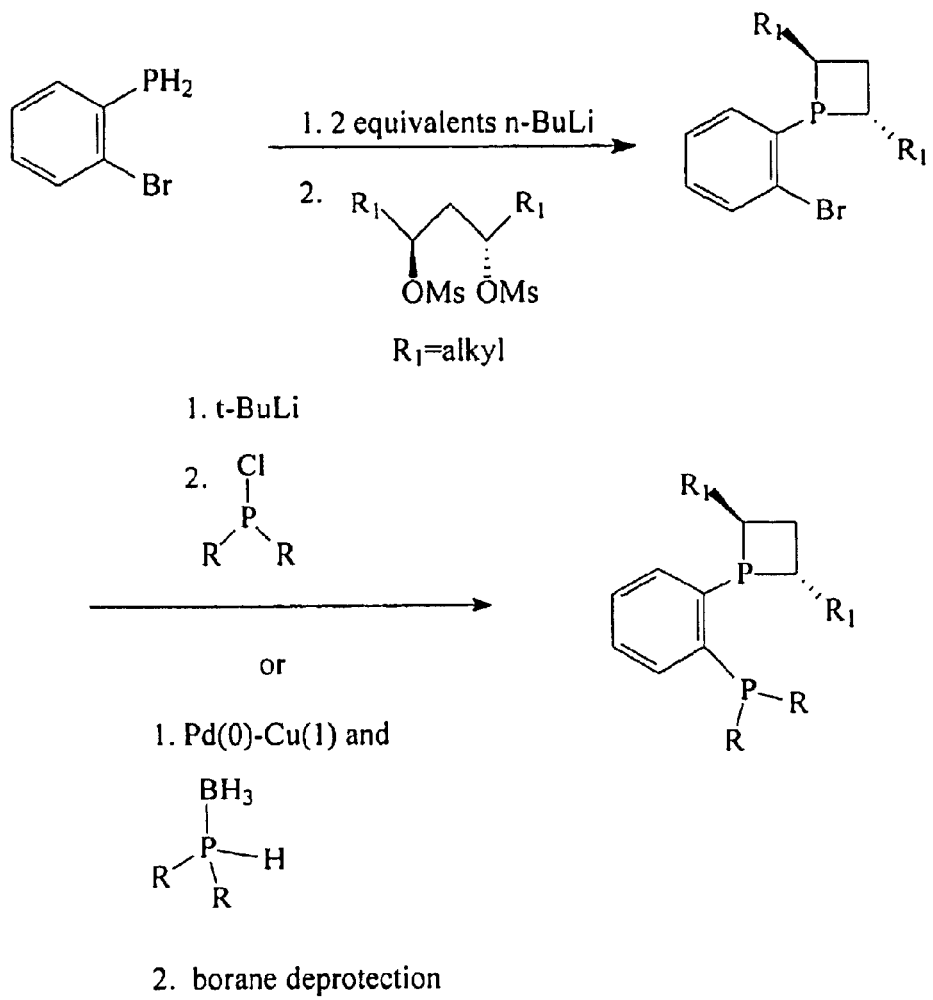
FIG. 12 shows a scheme for preparing another bisphosphine ligand.

Another compound can be synthesized via the route shown in FIG. 12, wherein Ms is mesylate and R is generally any bulky group as described above for the achiral phosphorus groups. Particularly useful R groups include tert-butyl, isopropyl, adamantyl, (1,1)-dimethylpropane, (1,1-diethylbutane), cyclopentyl or cyclohexyl.

Figure 13:
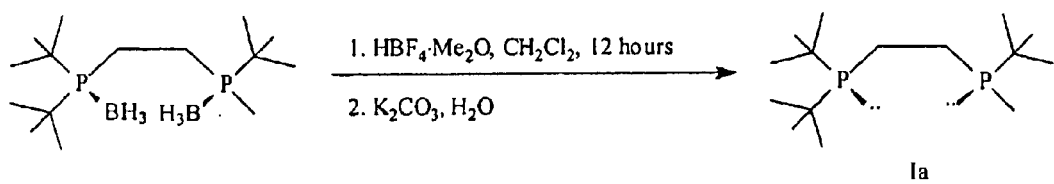
FIG. 13 shows a scheme for removing borane groups from an intermediate ligand to form a compound of Formula Ia.

Conditions can be used for borane removal or deprotection from the phosphorus atom of borane protected ligands, such as compounds shown in FIG. 9, that do not lead to racemization at the non-$C_2$-symmetric center to form compounds I, Ia, Ib, Ic, and IIa. The borane group can be removed by treating the phosphine borane ligand with $HBF_4 \cdot Me_2O$ followed by hydrolysis with $K_2CO_3$. For example, as shown in FIG. 13, the borane groups can be removed from an intermediate ligand to form a compound with the formula Ia.

Upon completion of borane removal, ligands of the general formulas I can be bound immediately to rhodium by reacting the ligand with $[Rh(norbornadiene)BF_4]_2$ to yield a catalyst with the Formula XIa:

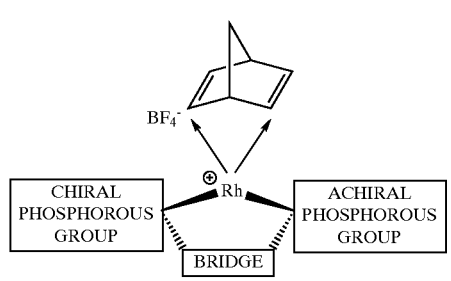

XIa wherein:
the achiral phosphorous group includes at least one achiral phosphorous atom having one bond to each of two identical atoms other than the bridge;
the chiral phosphorous group comprises at least one phosphorous atom, wherein the at least one phosphorous atom is chiral or the at least one phosphorous atom is bonded to a chiral substituent; and
the bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

Any suitable transition metal, actinide, or lanthanide and corresponding anion can be used to form the meta/non-$C_2$ bisphosphine complex shown as compound XIa. For example, the corresponding anion can alternatively be $PF_6-$, $SbF_6-$, $OTf-$, or $ClO_4-$.

Synthetic Route to BisP

Also shown in FIG. 9 is a synthesis method for the formation of BisP. Either enantiomer of compound IX can then easily be converted to either enantiomer of BisP, or the ligand Ia, as shown in FIG. 9. The difference in the synthesis of BisP and the ligand Ia is the use of either di-tert-butylphosphine borane in the synthesis of ligand Ia or tert-butylmethylphosphine borane in the synthesis of BisP, as the nucleophile that displaces the mesylate in the last step of the synthesis. In the synthesis of BisP, nucleophilic displacement creates yet another chiral center resulting in a reaction mixture that contains a 50:50 mixture of the chiral ligand and the meso ligand. The meso compound is easily separated from the chiral compound by column chromatography. In the case of the di-tert-butylphosphine borane addition, no further chiral centers are formed in the reaction so all of the material in the reaction mixture after addition is a single enantiomer chiral compound, Ia.

Asymmetric Transformations with Metal/Non-$C_2$-Symmetric Ligands

Metal/non-$C_2$-symmetric ligands of the general Formula VIII and XI can be used to catalyze hydrogenation and other asymmetric reactions. For example, compounds of the general Formula VII and XI can also be used as catalysts in transformations including, but not limited to, hydroformylation, π-allyl palladium coupling, hydrosilation, hydrocyanation, olefin metathesis, hydroacylation, and isomerization of allylamines.

In the case of asymmetric hydrogenation reactions, the metal/non-$C_2$-symmetric phospholanes can catalyze various substrates. For example, one useful complex is represented by the Formula XIa,
wherein the chiral group is

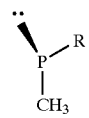

and the achiral group is

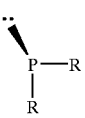

wherein R is tert-butyl, isopropyl, adamantyl, (1,1-dimethylpropane), (1,1-diethylbutane), cyclopentyl or cyclohexyl. Such complexes can be used to catalyze substrates, such as enamides, enol esters, and succinates, with general structural Formula X:

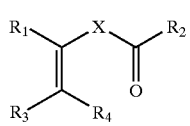

X wherein X is N, O, or C; $R_1$ is an alkyl, a carboxylic acid derivative, a carboxylic ester, or a nitrile; $R_2$ is an alkyl, an acetyl derivative, or a carboxylic acid; and $R_3$ is an alkyl or hydrogen, and $R_4$ is an alkyl identical to the alkyl in $R_3$ or hydrogen.

Metal/non-$C_2$-symmetric compounds typically bond to a substrate to be catalyzed through the center, M, which is bound to phosphorous atoms belonging to the chiral and achiral phosphorous groups of a compound having structural Formula XIb, its corresponding enantiomer, or solvates thereof,

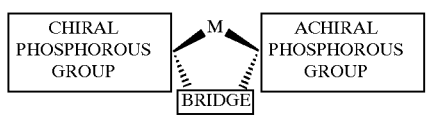

XIb wherein:

M is a transition metal, an actinide, or a lanthanide;

the achiral phosphorous group includes at least one achiral phosphorous atom having one bond to each of two identical atoms other than the bridge;

the chiral phosphorous group comprises at least one phosphorous atom, wherein the at least one phosphorous atom is chiral or the at least one phosphorous atom is bonded to a chiral substituent; and the bridge is a substituted or unsubstituted $C_{1-12}$ alkylene, aryl, heteroaryl, or ferrocene. Useful bridge moieties include a 1,2-divalent phenyl or a 2,3-divalent quinoxalinyl, each having from 0 to 4 non-hydrogen substituents bonded to ring atoms; a 2,3-divalent pyridinyl having from 0 to 3 non-hydrogen substituents bonded to ring atoms; and a 2,3-divalent pyrazinyl having from 0 to 2 non-hydrogen substituents bonded to ring atoms.

A solvate of the Formula XIb includes compounds having one or more solvent molecules bonded to the M center. The solvent molecules include, but are not limited to, MeOH, THF, ethanol, isopropanol, acetonitrile, methylene chloride, benzene, toluene, water, ethyl acetate, dioxane, carbon tetrachloride, DMSO, DMF, DMF/water mixtures, supercritical carbon dioxide, alcohol/water mixtures or any other suitable solvent.

Figure 14:
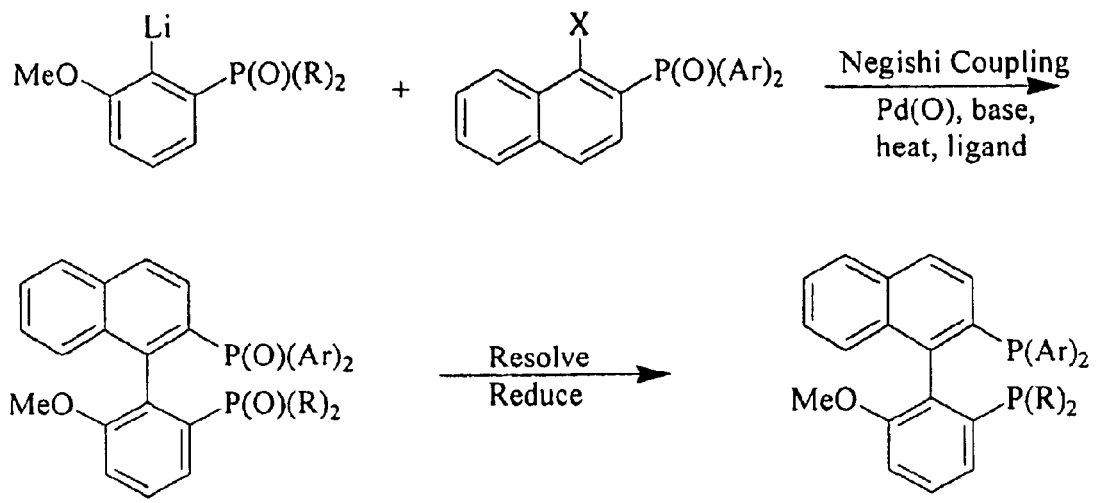
FIG. 14–FIG. 16 show schemes for preparing 2,2'-bisphosphinebiaryl ligands.
Figure 15:
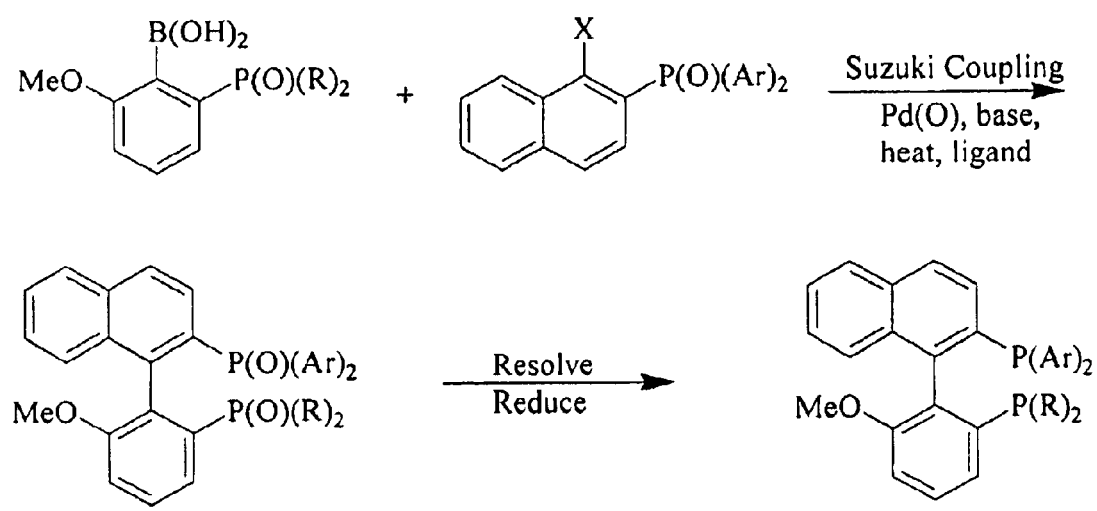
Figure 16:
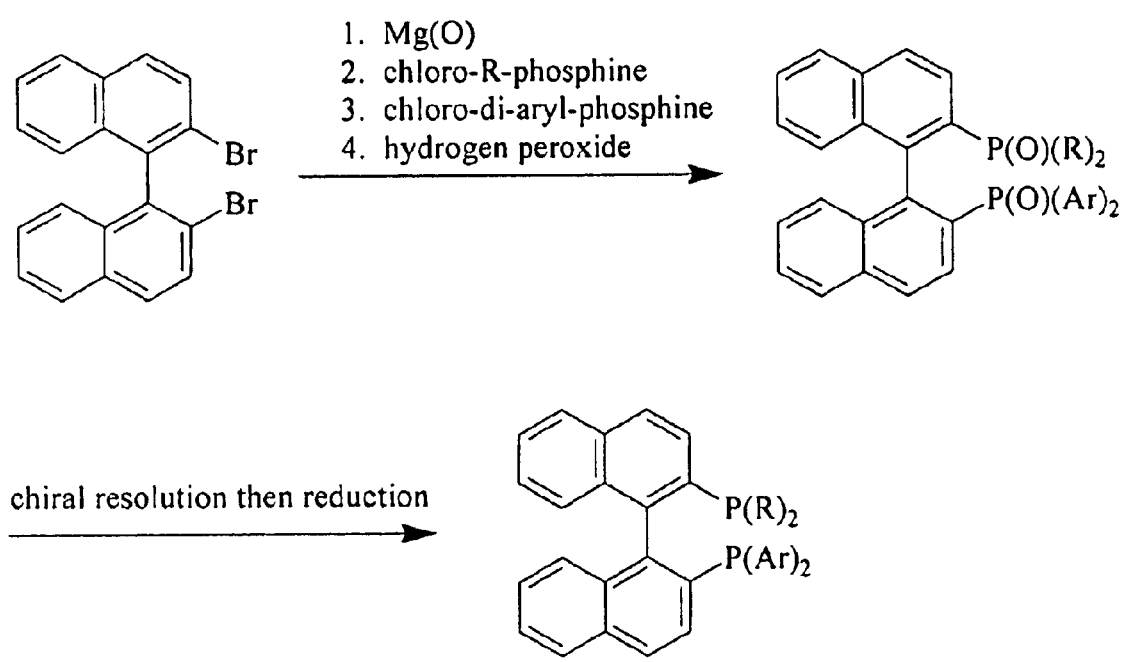

Preparation of 2,2'-bisphosphinebiaryl Ligands 2,2'-bisphosphinebiaryl ligands can be prepared using processes shown in FIG. 14–FIG. 16. In each of the schemes, X is halogen, Ar is aryl (e.g., phenyl) and R is a substituent exhibiting steric hindrance at least as great as an isopropyl group, and includes isopropyl, tert-butyl, 1,1,3,3-tetramethylbutyl, $C_{5-15}$-cycloalkyl, such as cyclopentyl and cyclohexyl; 1-methyl-cyclopentyl, 1-methyl-cyclohexyl, 1-ol-$C_{5-15}$-cycloalkyl, dialkylamino, diarylamino, 1-alkoxy-$C_{5-15}$-cycloalkyl, adamantyl, 1,1-dimethylpropyl, 1,1-diethylbutyl, and a bulky aryl group such as substituted phenyl.

EXAMPLES

The following examples are intended as illustrative and non-limiting, and represent specific embodiments of the present invention.

Non-$C_2$-Symmetric Ligands and Catalysts General Procedures

Materials

THF was distilled from sodium prior to use or THF (anhydrous, 99.9%) was used as needed from Aldrich Sure-Seal bottles supplied by Aldrich Chemical Company. Dichloromethane (anhydrous, 99.8%) and diethyl ether (anhydrous, 99.8%) were used as needed from Aldrich Sure-Seal bottles supplied by Aldrich Chemical Company. Methyl sulfoxide (DMSO, A.C.S. reagent, 99.9%), sodium borohydride (995), methanesulfonyl chloride (99.5%+), tert-butylmagnesium chloride (2.0 M diethyl ether), borane-methylsulfide complex (approximately 10–10.2 M), phosphorous trichloride (98%), lithium aluminum hydride (powder, 95%), and n-BuLi (2.5M hexanes) were obtained from Aldrich Chemical Company. N-chloroacetyl-(S)-(–)-4-benzyl-2-oxazolidinone was prepared according to literature procedures described in Tang, J. S., Verkade J. G. *J. Org. Chem.* 1996;61:8750–8754.

Nuclear Magnetic Resonance

400 MHz $^1$H NMR, 100 MHz $^{13}$C NMR, and 162 MHz $^{31}$P NMR spectra were obtained on "Barton"—a Varian Unity+400 (Inova400 after 08/15/00) spectrometer equipped with an Auto Switchable 4-Nuclei PFG probe, two RF channels, and a SMS-100 sample changer by Zymark. Spectra were generally acquired near room temperature (21° C.), and standard autolock, autoshim, and autogain routines were employed. Samples are usually spun at 20 Hz for 1D experiments. $^1$H NMR spectra were acquired using 45-degree tip angle pulses, 1.0 second recycle delay, and 16 scans at a resolution of 0.25 Hz/point. The acquisition window was typically 8000 Hz from +18 to –2 ppm (Reference TMS @ 0 ppm), and processing was with 0.2 Hz line broadening. Typical acquisition time is 80 seconds. Regular $^{13}$C NMR spectra were acquired using 45-degree tip angle pulses, 2.0 second recycle delay, and 2048 scans at a resolution of 1 Hz/point. Spectral width was typically 25 KHz from +235 to –15 ppm (Reference TMS @ 0 ppm). Proton decoupling was applied continuously, and 2 Hz line broadening was applied during processing. Typical acquisition time is 102 minutes. $^{31}$P NMR spectra were acquired using 45-degree tip angle pulses, 1.0 second recycle delay, and 64 scans at a resolution of 2 Hz/point. Spectral width was typically 48 KHz from +200 to –100 ppm (Reference 85% Phosphoric Acid @ 0 ppm). Proton decoupling was applied continuously, and 2 Hz line broadening was applied during processing. Typical acquisition time is 1.5 minutes.

High Performance Liquid Chromatography

High Performance Liquid Chromatography (HPLC) was performed on a series 1100 Hewlett Packard (now Agilent Technologies) instrument equipped with a manual injector, quaternary pump, and a UV detector. The LC was PC controlled using HP Chemstation Plus Software. Reverse phase HPLC was performed with a 150×4.6 mm BDS-Hypersil-C18 column supplied by Keystone Scientific Incorporate Reverse phase chiral HPLC was performed using a Chiracel OJ-R column supplied by Chiral Technologies. Normal Phase chiral HPLC was performed a Chiracel OD-H column supplied by Chiral Technologies.

Example 1

Synthesis of di-tert-butyl-phosphane borane $PCl_3$ (3.94 g, 2.5 mL, 0.029 mole) was dissolved in 75 mL anhydrous THF in a 250-mL round bottom flask under $N_2$ and then cooled to 0° C. with an ice bath. The tert-butylmagnesium chloride (29 mL, 0.058 mole, 2.0 M in diethyl ether) was added dropwise via syringe, and then the reaction was stirred 1.5 hours at 0° C. Lithium aluminum hydride (1.1 g, 0.029 mole) was then delivered to the reaction as a dry powder in portions over 20 minutes. After the addition, borane methylsulfide (2.9 mL, 0.029 mole 10.0 M solution) was delivered via syringe. After stirring overnight, the reaction was cooled to 0° C. and then quenched cautiously with 150 mL 1N HCl. The reaction mixture was poured into a separatory funnel, and the organic layer was separated. The aqueous layer was extracted with 2×100 mL Et$_2$O and then the combined organics were dried over MgSO4. The volatiles were then removed on a rotary evaporator at reduced pressure. The crude product was passed through a plug of silica gel using 3% ethyl acetate/hexane to yield the title compound with sufficient purity for subsequent chemistry. $^1$H NMR (400 MHz, CDCl$_3$) δ 0.0–0.9 (m, 3 H), 1.28 (d, J$_{H-P}$=13.4 Hz, 18 H), 3.65 (dm, $^J$H-P=351.2 Hz, 1 H); $^{31}$P NMR (162 MHz, CDCl$_3$) δ49.0 ppm (br m).

Example 2

Synthesis of tert-butyl-methyl-phosphane borane

Dichloromethylphosphine (25 g, 0.214 mole) was poured out of an ampule into a 3-neck 1000-mL flask equipped with an addition funnel while blowing N$_2$ through the flask. Nitrogen degassed anhydrous Et$_2$O (350 mL) was immediately poured into the flask and then the flask was sealed with a septum. The solution was cooled to 0° C. and then borane methylsulfide (21.4 mL, 0.214 moles, 10.0 M solution) was delivered to the solution via syringe. After stirring for 20 minutes, tert-butylmagnesium chloride (107 mL, 0.214 mole, 2.0 M in ethyl ether) was delivered via the addition funnel over a period of one hour while maintaining the reaction solution at 0° C. During the addition, a white precipitate formed which persisted during stirring for 45 minutes after the addition. Lithium aluminum hydride was then delivered to the reaction as a dry powder in portions over 20 minutes while maintaining the reaction temperature at 0° C. After the addition the reaction was warmed to room temperature and then stirred overnight. It was then cooled to 0° C. and quenched cautiously with 400 mL $^1$N HCl. The organic layer was separated, and then the aqueous layer was extracted with 100 mL Et$_2$O. The combined organics were combined and washed with $^1$N HCl and brine and then dried over MgSO$_4$. Removal of the solvent invacuo yielded 23.4 g/93% of the title compound with sufficient purity for subsequent chemistry. $^1$H NMR (400 MHz, CDCl$_3$) δ0–0.8 (m, 3 H), 1.17 (d, J$_{H-P}$=14.65 Hz, 9 H), 1.28 (dd, J=4.64 Hz, J=5.86 Hz, 3 H), 4.38 (dm, J$_{H-P}$=355.2 Hz, 1 H); $^{31}$P NMR (162 MHz, CDCl$_3$) δ12.0 (br m).

Example 3

Synthesis of (S)4-Benzyl-3-[2-((R)-tert-butyl-methyl-phosphanyl)-ethanoyl]-oxazolidin-2-one and (S)-4-Benzyl-3-[2-((S)-tert-butyl-methyl-phosphanyl)-ethanoyl]-oxazolidin-2-one N-Chloroacetyl-(S)-(−)-4-benzyl-2-oxazolidinone (6.39 g, 0.0254 mole) was placed in a 250-mL round bottom flask. (+/−)-tert-butyl-methyl-phosphane borane was added to the flask along with 75 mL DMSO. Potassium carbonate (17.5 g, 0.127 mole) was added in one portion and the reaction was placed under N$_2$. The reaction was heated to 55° C. in an oil bath and stirred for one hour. The resulting solution was red and K$_2$CO$_3$ was not completely dissolved in solution. The reaction was cooled to room temperature and then was poured into 500 mL $^1$N HCl which had been chilled to 0° C. Ethyl acetate (300 mL) was added and the biphasic solution was shaken briskly in a separatory funnel. The organic layer was separated and then the aqueous layer was extracted with 100 mL ethyl acetate. The combined organic layers were then washed successively with distilled water and then brine. The organic layer was dried over MgSO$_4$ and the solvent was removed invacuo. The crude white oily product was triturated with 2×75 mL warm hexane to remove excess phosphine and then the resulting white solid was dissolved in 30 mL hot ethyl acetate and allowed to cool to room temperature. Upon cooling, crystals formed. The crystals were collected on filter paper and then washed with 30 mL hexane. Crystals then formed in the filtrate. The diastereomeric ratio of the crystals on the filter paper was 92 ((S,R) isomer):8 ((S,S) isomer) and they weighed 1.17 g. After collecting the crystals from the filtrate on filter paper and washing with hexane it was found that the diastereomeric ratio of these crystals was 8 ((S,R) isomer):92 ((S,S) isomer) and then weighed 1.20 g. Successive recrystallization of both diastereomers with EtOAc/hexane yielded compounds with diastereomeric purity exceeding 99%. It is also possible to separate the (S,R) and (S,S) diastereomers via column chromatography over silica gel (15% ethyl acetate, hexane) collecting the (S,R) isomer at R$_f$=0.38 and the (S,S) isomer at R$_f$=0.28. Stereochemistry of the chirogenic phosphorous atom of each diastereomer was assigned by analogy using a comparison of elution orders of the enantiomers of Bis-P boranes made from this route with the elution orders of Bis-P boranes described in Imamoto, T. et al., supra., 1998. (S)-4-Benzyl-3-[2-((R)-tert-butyl-methyl-phosphanyl)-ethanoyl]-oxazolidin-2-one $^1$H NMR (400 MHz, CDCl$_3$) δ−0.2–0.8 (m, 3 H), 1.22 (d, J$_{H-P}$=14.7 Hz, 9 H), 1.43 (d, J$_{H-P}$=9.89 Hz, 3 H), 2.80 (m, 2 H), 3.36 (dd, J=3.38 Hz, J=13.5 Hz, 1 H), 4.15 (dd, J=2.17 Hz, J=8.92 Hz, 1 H), 4.26 (dd, J=8.68 Hz, J=8.68 Hz, 1 H), 4.34 (dd, J=9.16 Hz, J=12.18 Hz, 1 H), 4.68 (m, 1 H), 7.22–7.36 (m, 5 H); $^{13}$C NMR (100 MHz, CDCl$_3$) δ6.6 (d, J$_{C-P}$=33.6 Hz), 24.9, 28.1 (d, J$_{C-P}$=20.6 Hz), 38.2, 56.1, 66.3, 127.4, 129.2 (d, J$_{C-P}$=46.5 Hz), 135.4, 154.0, 167.5; $^{31}$P NMR (162 MHz, CDCl$_3$) δ27.8 (br m). (S)-4-Benzyl-3-[2-((S)-tert-butyl-methyl-phosphanyl)-ethanoyl]-oxazolidin-2-one: $^1$H NMR (400 MHz, CDCl$_3$) δ−0.2–0.8 (m, 3 H), 1.24 (d, J$_{H-P}$=14.47 Hz, 9 H), 1.45 (d, J$_{H-P}$=9.89 Hz, 3 H), 2.76 (dd, J=10.6 Hz, J=10.6 Hz, 1 H), 3.21 (dd, J=13.3 Hz, J=13.3 Hz, 1 H), 3.50 (dd, J=3.6 Hz, J=13.8 Hz, 1 H), 3.94 (dd, J=10.1 Hz, J=12.8 Hz, 1 H), 4.14–4.22 (m,2 H), 4.71 (m, 1 H), 7.23–7.28 (m, 3 H), 7.31–7.35 (m, 2 H); $^{13}$C NMR (100 MHz, CDCl$_3$) δ8.0 (d, J$_{C-P}$=30 Hz), 24.9, 27.9 (d, J$_{C-P}$=22 Hz), 29.0 (d, J$_{C-P}$=30 Hz), 38.0, 55.8, 66.2, 127.3, 129.0, 136.0, 154.0, 168.0; $^{31}$P NMR (162 MHz, CDCl$_3$) δ31.2 (br m).

Example 4

Synthesis of (R)-2-(tert-butyl-methyl-phosphanyl)-ethanol (S)-4-Benzyl-3-[2-((R)-tert-butyl-methyl-phosphanyl)-ethanoyl]-oxazolidin-2-one was dissolved in 60 mL anhydrous THF and then cooled to 0° C. in a 250-mL round bottom flask. NaBH$_4$ was added in one portion along with 15 mL distilled water. The reaction foamed after addition and when foaming was complete the reaction was warmed to room temperature and stirred overnight whereupon the reaction was quenched with 50 mL 2N HCl. The reaction was poured into a separatory funnel and 30 mL ethyl acetate was added. The organic layer was separated after shaking and then the aqueous layer was extracted with 2×50 mL ethyl acetate. The organic layers were combined and dried over MgSO$_4$ and then the volatiles were removed invacuo. The crude product was passed through a plug of silica gel using 25% ethyl acetate/hexane and after removing the volatiles in vacuo, 1.651 g/97.1% of the title compound was isolated. The (S) isomer can be synthesized via the same procedure starting from (S)-4-benzyl-3-[2-((S)-tert-butyl-methylphosphanyl)-ethanoyl]-oxazolidin-2-one. $^1$H NMR (400 MHz, CDCl$_3$) δ1.14 (d, J$_{H-P}$=13.74 Hz, 9 H), 1.25 (d, J$_{H-P}$=9.9 Hz, 3 H), 1.81–1.92 (m, 2 H), 2.42 (br s, 1 H); 3.92 (dt, J=15.2 Hz, J=6.3 Hz, 2 H); $^{13}$C (100 MHz, CDCl$_3$) δ6.3 (d, J$_{C-P}$=35.1 Hz), 24.6 (d, J=32.1 Hz), 24.9, 27.2 (d, J$_{C-P}$=35.1 Hz), 57.8; $^{31}$P (162 MHz, CDCl$_3$) δ23.2 (br m).

Example 5

Synthesis of Methanesulfonic Acid 2-((R)-tert-butyl-methyl-phosphanyl borane)-ethyl ester The (R)-2-(tert-butyl-methyl-phosphanyl)-ethanol (1.127 g, 6.957 mmol) was dissolved in 10 mL pyridine and cooled to 0° C. Methanesulfonyl chloride (0.59 mL, 7.65 mmol) was added dropwise via syringe. After one hour white salts had precipitated from the reaction solution. The reaction was then quenched with 50 mL distilled water. The reaction mixture was poured into a separatory funnel and the aqueous layer was extracted with 2×50 mL Et$_2$O. The combined organics were dried over MgSO$_4$ and then the volatiles were removed in vacuo yielding 1.553 g/93% of the mesylate product which was subjected to no further purification. The (S) isomer can be synthesized via the same procedure starting from (S)-2-(tert-butyl-methyl-phosphanyl)-ethanol. $^1$H NMR (400 MHz, CDCl$_3$) δ0.0–0.8 (br m), 1.17 (d, J$_{H-P}$=14.2 Hz, 9 H), 1.30 (d, J$_{H-P}$=9.9 Hz, 3 H), 1.90 (br s, 1 H), 2.08 (dt, J=10.9 Hz, J=7.5 Hz, 2 H), 3.05 (s, 3 H), 4.41–4.59 (m, 2 H); $^{31}$P NMR (162 MHz, CDCl$_3$) δ25.5 (br m).

Example 6

Synthesis of (R,R)-1,2-Bis(tert-butyl-methyl-phosphanyl borane) ethane

Methanesulfonic acid 2-((R)-tert-butyl-methyl-phosphanyl borane)-ethyl ester (536 mg, 2.232 mmol) was dissolved in 7 mL anhydrous THF in a 50-mL round bottom flask under N$_2$. The solution was cooled to –78° C. with a dry ice/acetone bath with stirring. In a separate 25-mL round bottom flask was dissolved (+/–)-tert-butyl-methyl-phosphane borane. This solution was placed under N$_2$ and then cooled to –78° C. n-BuLi (1.07 mL, 2.678 mmol, 2.5 M in hexane) was added dropwise via syringe to the (+/–)-tert-butyl-methyl-phosphane borane solution. The reaction was stirred for 20 minutes at –78° C. and then the solution was taken up in a syringe and delivered to the mesylate solution over 30 seconds. The reaction was stirred 20 minutes at –78° C. and then warmed to room temperature and stirred overnight. TLC (25% ethyl acetate/hexane) showed two products with R$_f$=0.49 (meso Bis-P) and R$_f$=0.38 (Bis-P). Column chromatography over silica gel eluting first with 7% ethyl acetate/hexane and increasing the gradient eventually to 25% ethyl acetate/hexane yielded 130 mg/44.5% meso compound and 147 mg/50.3% Bis-P (>99% e.e. of the (R,R) isomer). The (S,S) isomer can be synthesized via the same procedure starting from Methanesulfonic acid 2-((S)-tert-butyl-methyl-phosphanyl borane)-ethyl ester. Enantiomeric purity was determined by chiral HPLC using a Chiracel OD-H column (10 mm, 4.6×250 mm), mobile phase Hexanes:IPA:TFA 95:5:0.1, flow rate of 0.5 mL/min, and RI detection at 1/16 range. The (S,S) isomer was observed at 17.9 minutes and the (R,R) isomer was observed at 12.0 minutes. Spectral data was identical to that described in Imamoto T., et al., supra., 1998.

Example 7

Synthesis of 1-(Di-tert-butyl-phosphanyl borane)-((R)-2-tert-butyl-methyl-phosphanyl borane) ethane Methanesulfonic acid 2-((R)-tert-butyl-methyl-phosphanyl borane)-ethyl ester (660 mg, 2.75 mmol) was dissolved in 7 mL anhydrous THF in a 50-mL round bottom flask under N$_2$. The solution was cooled to –78° C. with a dry ice/acetone bath. In a separate 25-mL round bottom flask was dissolved di-tert-butyl-phosphane borane (528 mg, 3.30 mmol). This solution was placed under N$_2$ and then cooled to –78° C. n-BuLi (1.32 mL, 3.30 mmol, 2.5 M in hexane) was added dropwise via syringe to the di-tert-butyl-phosphane borane solution. The reaction was stirred for 20 minutes at –78° C. and then the solution was taken up in a syringe and delivered to the mesylate solution over 30 seconds. The reaction was stirred 20 minutes at –78° C. and then warmed to room temperature and stirred overnight. TLC (25% ethyl acetate/hexane) showed title product with R$_f$=0.53. Column chromatography over silica gel (10% ethyl acetate/hexane) yielded 370 mg/44% of the title compound. The (S) isomer can be synthesized via the same procedure starting from Methanesulfonic acid 2-((S)-tert-butyl-methyl-phosphanyl borane)-ethyl ester. $^1$H NMR (400 MHz, CDCl$_3$) δ–0.2–0.8 (br m, 3 H), 1.05–1.30 (br m, 30 H), 1.50–1.70 (br m, 2 H), 1.75–2.05 (br m, 2 H); $^{31}$P NMR (162 MHz, CDCl$_3$) δ30.0 (br m), 47.0 (br, m).

Example 8

Synthesis of 1-(Di-tert-butyl-phosphanyl-fluoro borane)-((R)-2-tert-butyl-methyl-phosphanyl-fluoro borane) ethane 1-(Di-tert-butyl-phosphanyl borane)-((R)-2-tert-butyl-methyl-phosphanyl borane) ethane (60 mg, 0.20 mmol) was dissolved in 2 mL dry CH$_2$Cl$_2$ in a 100 mL Schlenk flask. Excess HBF$_4$.Et$_2$O (0.6 mL, 4 mmol) was added dropwise by a syringe. Gas bubbles appeared upon the addition. The reaction was stirred for 12 hours till the TLC showed a complete disappearance of the starting material and the volatiles were then removed under reduced pressure. The residue was washed with Et$_2$O 3×30 mL and yielded white powdery title compound and was used without further purification. (67 mg, 100%) $^1$H NMR (400 MHz, CD$_2$Cl$_2$) δ1.18 (m, 9 H), 1.45 (d, J=18.5 Hz, 9 H), (m, 9 H+3H), 2.00 (dd, J$_1$=5.86Hz, J$_2$=11.04 Hz, 4 H), 3.49 (m, 2 H+2H); $^{31}$P NMR (162 MHz, CD$_2$Cl$_2$)δ29.9 (d, J$_2$=41.53 Hz), 49.37 (d, J$_2$=41.53 Hz). $^{19}$F NMR (376 MHz, CD$_2$Cl$_2$) δ–156.0 (br, w), –148.9 (br, vs).

Example 9

Synthesis of 1-(Di-tert-butyl-phosphanyl)-((S)-2-tert-butyl-methyl-phosphanyl) ethane 1-(Di-tert-butyl-phosphanyl-fluoro borane)-((R)-2-tert-butyl-methyl-phosphanyl-fluoro borane) ethane (60 mg, 0.18 mmol) was dissolved in 10 mL dry CH$_3$OH in a flask inside Dry Box. Heat was needed for a complete dissolution. DABCO 40 g, 0.36 mmol, 1 equiv.) was added to the solution and a white precipitate appeared. The reaction was stirred for 3 hours and then filtered. The volatiles were then removed under reduced pressure to give the title compound as a paste. (49 mg, 100%). $^1$H NMR $^{31}$P NMR shows the paste to be the title compound. The filtrate was collected and NMR shows it to be DABCO-BH$_2$F.

Example 10

Synthesis of ((tert-Bu)$_2$P(CH$_2$)$_2$P(Me)(tert-Bu))$_2$Rh$_2$Cl$_2$ or Bis-(R)-1-(di-tert-butyl-phosphanyl)-(2-tert-butyl-methyl-phosphanyl) ethane-Rh-di-Chloride In a glove box, Rh$_2$ (COD) $_2$Cl$_2$ is dispersed in MeOH as an orange slurry and MeOH solution of 1-(di-tert-butylphosphanyl)-((S)-2-tert-butyl-methyl-phosphanyl) ethane is added drop-wise while the reaction is vigorously stirred. The slurry clears after stirring for 2 hours, and the solution is filtered after another hour. The red-orange MeOH solution is concentrated under reduced pressure and allowed to sit at room temperature in a $N_2$ box to let the solvent evaporate slowly. The title complexes are obtained from the solution after two days as yellowish crystals. The mother solution is further evaporated to give another batch of crystals. The (S, S)-Dimer can be synthesized via the same route from the 1-(di-tert-butyl-phosphanyl)-((S)-2-tert-butyl-methyl-phosphanyl) ethane solution.

Example 11

Asymmetric hydrogenation of enamides with ((tert-Bu)$_2$P(CH$_2$)$_2$P(Me)(tert-Bu))$_2$Rh$_2$Cl$_2$ ((tert-Bu)$_2$P(CH$_2$)$_2$P(Me)(tert-Bu))$_2$Rh$_2$Cl$_2$ was used to catalyze the asymmetric hydrogenation of four enamides, which are represented by Formula X above, in which X is nitrogen, $R_2$ is methyl, $R_4$ is hydrogen and (a) $R_1$ is carboxy, $R_3$ is hydrogen (2-acetylamino-acrylic acid); (b) $R_1$ is methoxycarbonyl, $R_3$ is hydrogen (2-acetylamino-acrylic acid methyl ester); (c) $R_1$ is carboxy, $R_3$ is phenyl (2-acetylamino-3-phenyl-acrylic acid); and (d) $R_1$ is methoxycarbonyl, $R_3$ is phenyl (2-acetylamino-3-phenyl-acrylic acid methyl ester).

In a glove box, ((tert-Bu)$_2$P(CH$_2$)$_2$P(Me)(tert-Bu)) 2Rh$_2$Cl$_2$ (4.1 mg, 0.005 mmol) was dissolved in 2 mL MeOH, followed by addition of AgBF$_4$ (1.9 mg, 0.10 mmol, 2 equiv.). The solution turned from pale yellow to yellow with gray precipitates. After being stirred for 20 minutes the solution was filtered into a high-pressure tube containing a stir bar and one of the enamides (1 mmol, 100 equiv.). Another 3 to 5 mL MeOH was added and the solution generally turned lighter upon the addition of the enamide substrate. The vessel was then put under H$_2$ of 30 to 40 Psig and stirred at room temperature. After the reaction was finished, the vessel was then take out of the glove box, and an aliquot of the reaction solution was taken from the vessel and analyzed directly or after work up to determine enantiomeric excess of the reaction product. Reaction of enamide (a) to form 2-acetylamino-propionic acid and reaction of enamide (b) to form 2-acetylamino-propionic acid methyl ester, yielded greater than 99% enantiomeric excess in both instances. Reaction of enamide (c) to form 2-acetylamino-3-phenyl-propionic acid and reaction of enamide (d) to form 2-acetylamino-3-phenyl-propionic acid methyl ester, yielded greater than 98% and 95% enantiomeric excess, respectively.

Example 12

Synthesis of tert-Butyldimethylphosphineborane

Tert-butylphosphine dichloride (10.0 g, 62.9 mmol) ampule was put into a hot water bath at 60° C. until the contents was completely melted. It was then decanted rapidly into a Schlenk flask under a flow of nitrogen. Dry THF (20 mL) from a Sure-Seal bottle was added to the flask and the solution was cooled to 0° C. Methylmagnesium bromide reagent (50 mL of a 3.0 M solution in diethyl ether, 150 mmol, 2.4 equiv.) was added over a period of 20 minutes via syringe. The reaction was stirred at 0° C. for one hour and then warmed to 25° C. and stirred for one hour. It was then cooled down to 0° C. and BH$_3$-SMe$_2$ complex (6.29 mL of a 10.0M reagent, 62.9 mmol, lequiv.) was added via syringe. The mixture was stirred at room temperature for 40 minutes and then cautiously poured into a mixture of 400 mL ice water, 40 mL conc. HCl, and 300 mL ethyl acetate. The aqueous phase was then extracted with ethyl acetate 200 mL×3 and then the combined organic phase was dried over MgSO$_4$. The solvent was then removed under reduced pressure to give 8.1 g (97%) of pure title compound. $^1$H NMR (CDCl$_3$): δ0.42 (q, 3H, J$_{H-B}$=96 Hz, BH$_3$,), 1.12 (d, 9H, J$_{H-P}$=16 Hz, tert-butyl), 1.19 (d, 6H, J$_{H-P}$=8 Hz, Me); $^{31}$P: δ21.3 (q. 1H, J=140 Hz).

Example 13

Synthesis of Methylene((R)-tert-butylmethylphosphine borane)(di-tert-butylphosphine borane) or Methylene((S)-tert-butylmethylphosphine borane)(di-tert-butylphosphine borane)

In a Schlenk flask was placed tert-butyldimethylphosphine borane (1.75 g, 9.62 mmol) and then the flask was purged with N$_2$. Dry THF (10 mL) was added and the solution was cooled to −78° C. Sec-BuLi solution (1.3 M solution in cyclohexane, 7.4 mL, 9.6 mmol, 1 equiv.) was added to the solution dropwise and the reaction was stirred for one hour. Di-tert-butylchlorophosphine (2.09 g, 11.5 mmol) was then added dropwise via syringe. The reaction was warmed to room temperature, heated to 45° C. for 2 hours, cooled to room temperature, and then stirred overnight. The reaction was cooled to 0° C. and then BH$_3$-SMe$_2$ (0.96 mL of a 10.0M reagent, 9.62 mmol, lequiv.) was added via syringe. The mixture was stirred at 0° C. for 40 minutes before it was quenched cautiously with 20 mL of 1N HCl solution. The aqueous phase was then extracted with ethyl acetate (20 mL×3) and the combined organic phase was dried over MgSO$_4$. The solvent was then removed under reduced pressure to give an oily residue. Column chromatography using 10% ethyl acetate in heptanes yielded 1.02 g (36%) of title compound. Analytical separation of the enantiomers may be accomplished using chiral HPLC (Chiracel OD-H with 2% Isopropyl alcohol in hexanes with flow rate of 0.5 ml/min, enantiomer retention times at 10 & 11 minutes, refractive index detection). $^1$H NMR (CDCl$_3$): δ0.59 (q, 6H, J$_{H-B}$=92 Hz, BH$_3$,), 1.19 (d, 9H, J$_{H-P}$=12 Hz, tert-butyl), 1.27 (d, 9H, J$_{H-P}$=12 Hz, tert-butyl), 1.34 (d, 9H, J$_{H-P}$=16 Hz, tert-butyl), 1.57 (d, 3H, J$_{H-P}$=8 Hz, Me), 1.89 (t, 2H, J$_{H-P}$=12 Hz, CH$_2$); $^{31}$P: δ32.3 (m), 49.1 (m).

Example 14

Synthesis of (2R, 5R)-1-Methyl-2.5-methyl-phospholane borane

Methylphosphine borane was distilled prior to use. The phosphine borane (0.495 g, 7.86 mmol) was then dissolved in 25 mL THF in a 100 mL round bottom flask under N$_2$ and cooled to −78° C. To this solution was added n-BuLi (6.3 mL of a 2.5M solution in hexane, 15.72 mmol) and the reaction was stirred for one hour. To this solution was added (2S, 5S)-hexanedimesylate (6.29 mmol, 1.72 g) dissolved in 10 mL THF via syringe. After addition, the reaction was warmed to room temperature and then stirred overnight. After a standard aqueous work-up and removal of volatiles at reduced pressure a yellow oil remained. This oil was subjected to column chromatography over silica gel (5% EtOAc/hexane, 10 mL fractions) yielding 222 mg (25%) of the desired product. $^1$H NMR (400 MHz, CDCl$_3$) δ0.0–0.8 (br m, 3 H), 1.10–1.23 (m, 9 H), 1.24–1.43 (m, 2 H), 1.87–2.01 (m, 1 H), 2.02–2.16 (m, 2 H); $^{13}$C NMR (100 MHz, CDCl$_3$) d 7.24 (d, J$_{C-P}$=29.8 Hz), 13.60 (d, J$_{C-P}$=2.3 Hz), 15.42 (d, J$_{C-P}$=4.6 Hz), 32.72 (d, J$_{C-P}$=37.4 Hz), 33.67 (d, J$_{C-P}$=35.9 Hz), 34.41, 34.86 (d, J$_{C-P}$=3.1 Hz); $^{31}$P NMR (162 MHz, CDCl$_3$) δ33.9 (br m).

Example 15

Synthesis of Methylene-((2R, 5R)-2,5-methyl-phospholane borane)(di-tert-butylphosphine borane)

To a 50 mL round bottom flask was dissolved (2R, 5R)-1-methyl-2,5-methyl-phospholane borane (0.694 mmol, 0.100 g) in THF and cooled to −78° C. To this solution was added sec-BuLi (0.89 mL of a 1.3M solution in cyclohexane, 1.18 mmol) producing a yellow solution. After stirring for 45 minutes, di-tert-butylchlorophosphine (0.26 mL, 1.39 mmol) was added via syringe and the yellow color dissipated immediately. The reaction was warmed slowly to room temperature and then BH$_3$-Me$_2$S (0.14 mL of a 10.0 M solution, 1.4 mmol) was added to the reaction via syringe and it was stirred overnight. After a standard aqueous work-up and removal of volatiles under reduced pressure, the crude yellow oil was subjected to column chromatography over silica gel (5% EtOAc/hexane) yielding 0.060 g (29%) of title compound. $^1$H NMR (400 MHz, CDCl$_3$) δ0.1–1.1 (br m), 1.18–1.34 (br m), 1.70–1.81 (m), 2.05–2.20 (m), 2.2–2.3 (m), 2.75–2.85 (m); $^{13}$C NMR (100 MHz, CDCl$_3$) δ10.47 (dd, J$_{C-P}$=16.8 Hz, J$_{C-P}$=13.7 Hz), 13.40 (d, J$_{C-P}$=2.28 Hz), 16.66 (d, J$_{C-P}$=6.1 Hz), 27.93 (d, J$_{C-P}$=2.3 Hz), 28.46 (d, J$_{C-P}$=2.3 Hz), 31.5 (d, J$_{C-P}$=30.5 Hz), 32.9 (d, J$_{C-P}$=25.2 Hz), 33.85 (dd, J$_{C-P}$=25.2 Hz, J$_{C-P}$=3.0 Hz), 33.99, 35.42, 37.41 (dd, J$_{C-P}$=36.6 Hz, J=4.6 Hz); $^{31}$P NMR (162 MHz, CDCl$_3$) δ43.0 (br m), 47.5 (br m).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. The disclosures of all articles and references, including patent applications and publications, are hereby incorporated by reference in their entirety for all purposes.

What is claimed is:

1. A non-C$_2$ symmetric bisphosphine ligand comprising an achiral phosphine group, a chiral phosphine group, and a bridge that links the achiral and chiral phosphine groups, the ligand represented by Formula I:

I

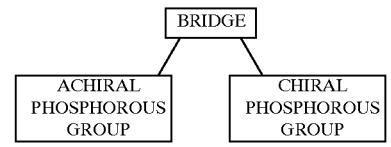

or corresponding enantiomers thereof, wherein:
the bridge is substituted or unsubstituted C$_{1–12}$ alkylene or aryl;
the achiral phosphine group is

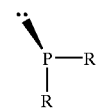

in which R is the same at each occurrence and is isopropyl, tert-butyl, 1,1-dimethylpropyl, 1,1-diethylbutyl, 1,1,3,3-tetramethylbutyl, cyclopentyl, 1-methyl-cyclopentyl, 1-methyl-cyclohexyl, 1-hydroxy-C$_{5–15}$-cycloalkyl, 1-alkoxy-C$_{5–15}$-cycloalkyl, adamantyl, dialkylamino, or diarylamino; and
the chiral phosphine group is

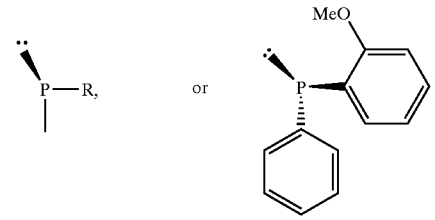

in which
R$_5$ is isopropyl, tert-butyl, 1,1-dimethylpropyl, 1,1-diethylbutyl, 1,1,3,3-tetramethylbutyl, 1-methyl-cyclopentyl, 1-methyl-cyclohexyl, C$_{5–15}$-cycloalkyl, 1-hydroxy-C$_{5–15}$-cycloalkyl, 1-alkoxy-C$_{5–15}$-cycloalkyl, dialkylamino, or diarylamino; and
R$_1$ is hydrogen, methyl, straight chain alkyl or substituted alkyl of up to twenty carbon atoms, alkoxy or substituted alkoxy of up to twenty carbon atoms, alkylamino, or arylamino, provided that R$_1$ and R$_5$ are different.

2. The ligand of claim 1, wherein the bridge is a substituted or unsubstituted 1,2-divalent phenyl.

* * * * *